(12) United States Patent
Fujiwara et al.

(10) Patent No.: US 8,469,881 B2
(45) Date of Patent: Jun. 25, 2013

(54) PRESSURE REDUCTION MECHANISM, PUNCTURE DEVICE, BLOOD ANALYSIS DEVICE, AND SENSOR MOUNTING MECHANISM

(75) Inventors: Masaki Fujiwara, Ehime (JP); Yohei Hashimoto, Ehime (JP)

(73) Assignee: Panasonic Corporation, Osaka (JP)

( * ) Notice: Subject to any disclaimer, the term of this patent is extended or adjusted under 35 U.S.C. 154(b) by 150 days.

(21) Appl. No.: 13/133,258

(22) PCT Filed: Oct. 15, 2009

(86) PCT No.: PCT/JP2009/005380
§ 371 (c)(1),
(2), (4) Date: Jun. 7, 2011

(87) PCT Pub. No.: WO2010/067501
PCT Pub. Date: Jun. 17, 2010

(65) Prior Publication Data
US 2011/0245635 A1    Oct. 6, 2011

(30) Foreign Application Priority Data

Dec. 9, 2008 (JP) .................................. 2008-313644
Dec. 12, 2008 (JP) .................................. 2008-317341

(51) Int. Cl.
*A61B 5/15* (2006.01)
(52) U.S. Cl.
USPC ............ 600/181; 606/182; 600/583; 600/584
(58) Field of Classification Search
USPC ............................ 600/583, 584; 606/181, 182
See application file for complete search history.

(56) References Cited

U.S. PATENT DOCUMENTS

| | | | | |
|---|---|---|---|---|
| 6,027,459 | A | * | 2/2000 | Shain et al. .................... 600/573 |
| 6,093,156 | A | | 7/2000 | Cunningham et al. |
| 6,210,420 | B1 | * | 4/2001 | Mauze et al. ................. 606/182 |

(Continued)

FOREIGN PATENT DOCUMENTS

| | | |
|---|---|---|
| EP | 1356768 | 10/2003 |
| JP | 11-206742 | 8/1999 |
| JP | 2000-245717 | 9/2000 |
| JP | 2004-000459 | 1/2004 |
| JP | 3144721 | 8/2008 |
| JP | 2008-206721 | 9/2008 |
| WO | 2008-075768 | 6/2008 |

OTHER PUBLICATIONS

Search report from E.P.O., mail date is Nov. 20, 2012.

*Primary Examiner* — Sean Dougherty
(74) *Attorney, Agent, or Firm* — Greenblum & Bernstein, P.L.C.

(57) ABSTRACT

Provided are a decompression mechanism capable of performing a desired pressure reduction by simple operation and having improved operability, a puncture device, a blood analysis device, and a sensor mounting mechanism. A needle puncturing device (100) is provided with: a piston (121) having at one end thereof an end part (121a) for forming a part of a sensor mounting mechanism (130) and at the other end an end part (121b) for slidably supporting a rod (112) of a lancet section (111); a cylinder (122) for slidably containing therein the end section (121b) of the piston (121); and packing (125) mounted to the inner periphery of the end part (121b) of the piston (121) and maintaining the air-tightness of the outer periphery of the rod (112). When the piston (121) is moved in the direction toward the cylinder (122) with a skin contact part (131) in contact with the skin, the volumes of an internal space (140) and a pressure reduction chamber (150) which are sealed by packing (123, 124) are increased to produce a reduced pressure.

12 Claims, 35 Drawing Sheets

U.S. PATENT DOCUMENTS

| | | |
|---|---|---|
| 6,261,245 B1 | 7/2001 | Kawai et al. |
| 6,730,046 B1* | 5/2004 | Hamamoto et al. .......... 600/583 |
| 7,131,984 B2 | 11/2006 | Sato et al. |
| 7,758,602 B2 | 7/2010 | Sato et al. |
| 2002/0169393 A1* | 11/2002 | Cunningham et al. ........ 600/573 |
| 2007/0232956 A1* | 10/2007 | Harman et al. ............... 600/573 |
| 2007/0282362 A1* | 12/2007 | Berg et al. ..................... 606/181 |
| 2009/0099478 A1* | 4/2009 | Cassells et al. ............... 600/583 |
| 2009/0299224 A1* | 12/2009 | Yoo ............................... 600/583 |
| 2010/0042016 A1 | 2/2010 | Akiyama |
| 2010/0228149 A1 | 9/2010 | Fujmura et al. |

\* cited by examiner

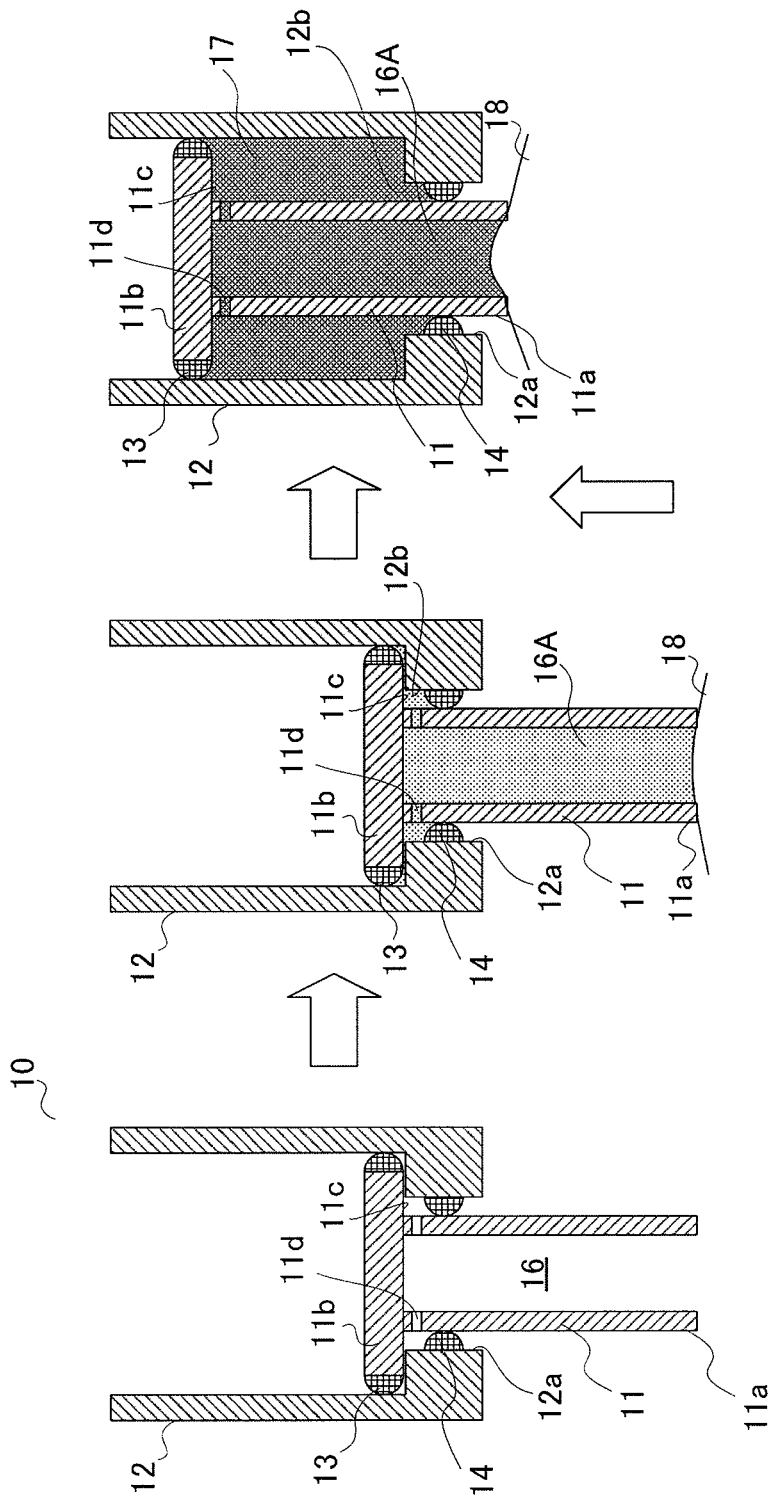

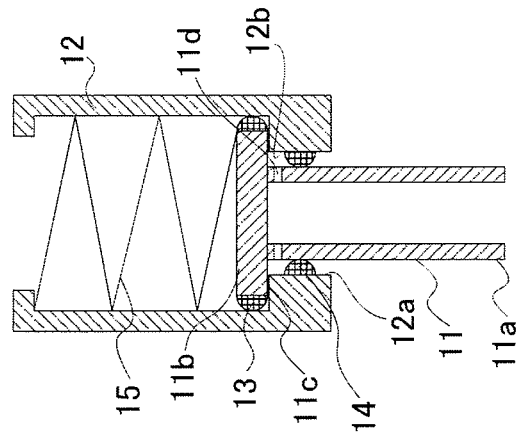
FIG.3F
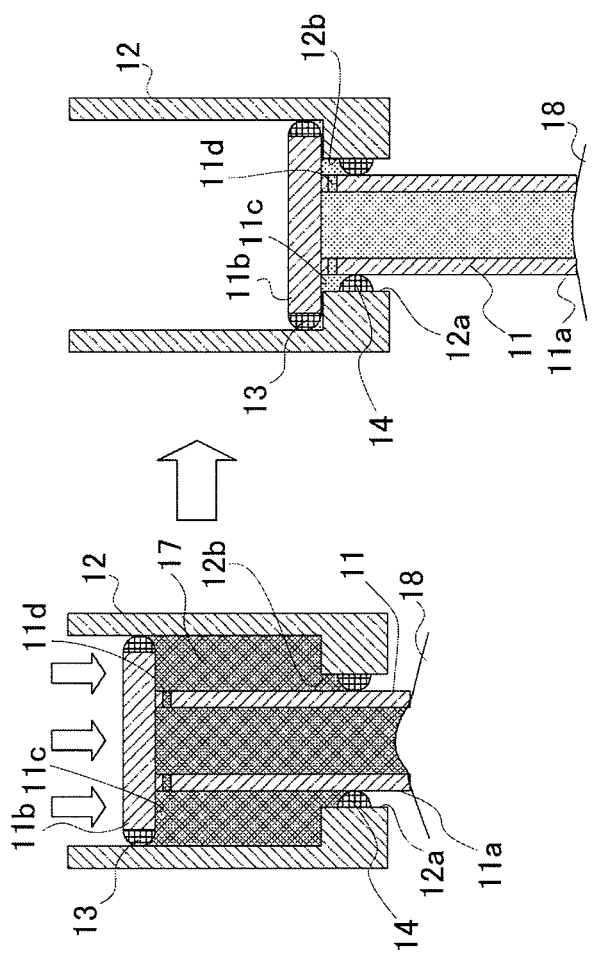
FIG.3E
FIG.3D

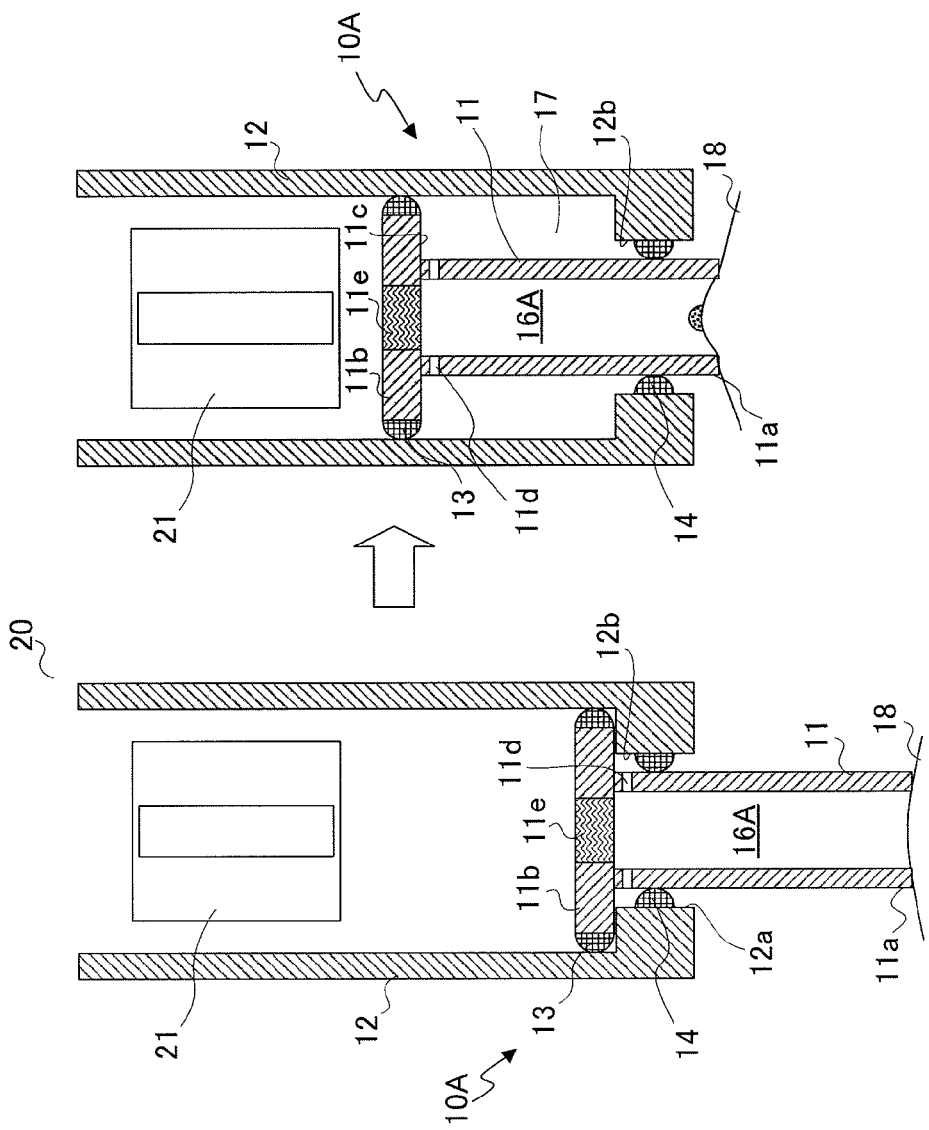

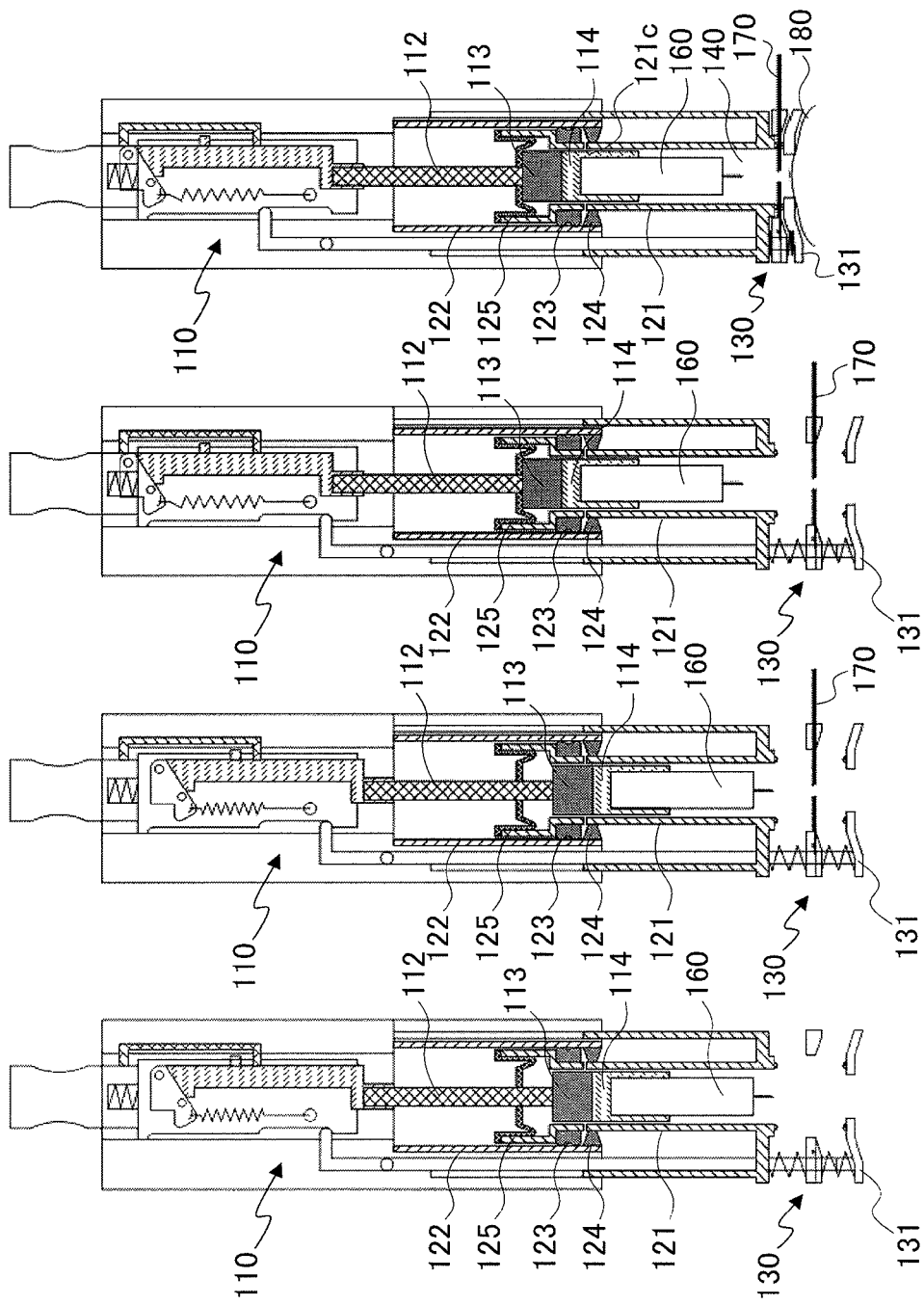

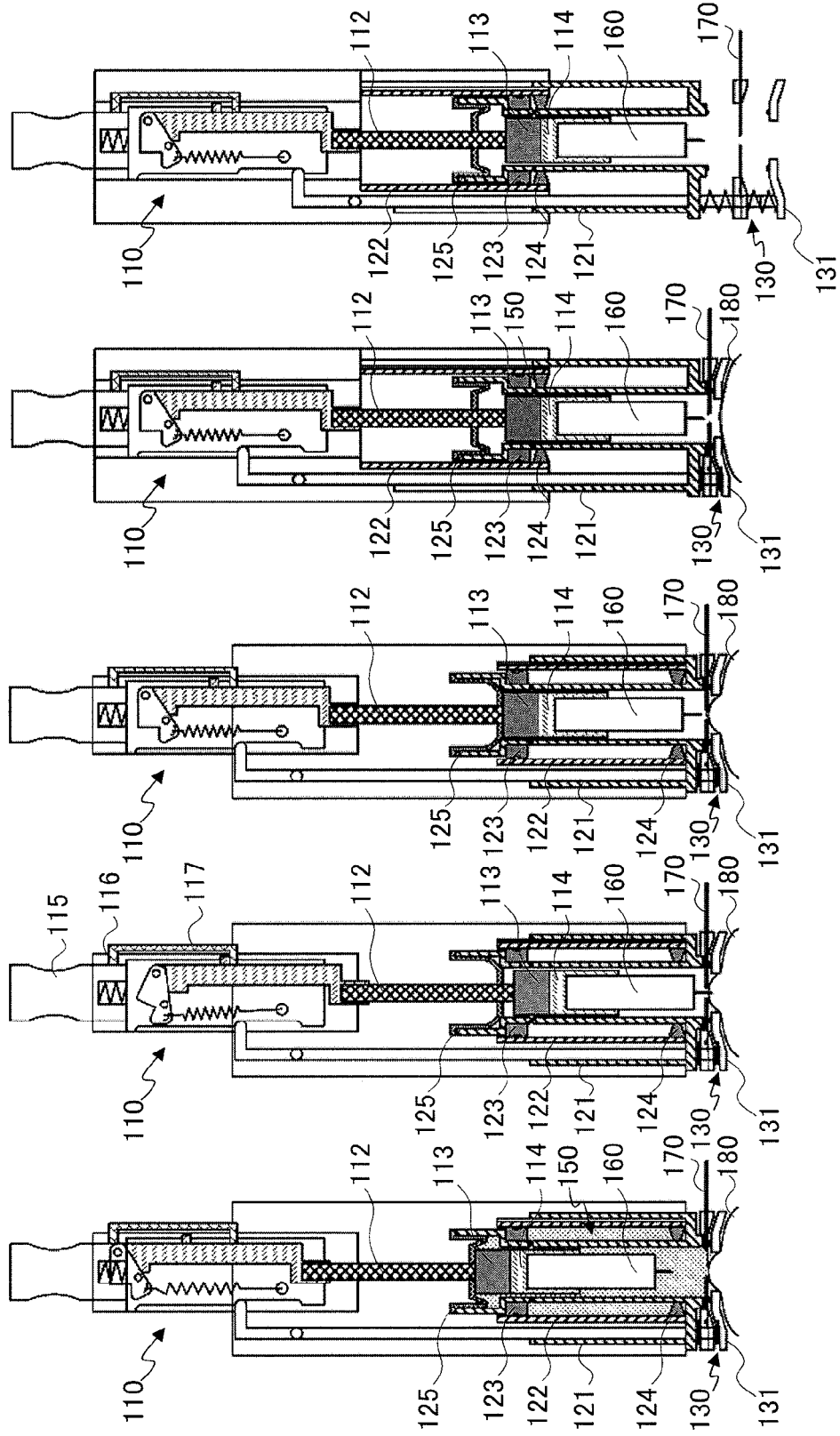

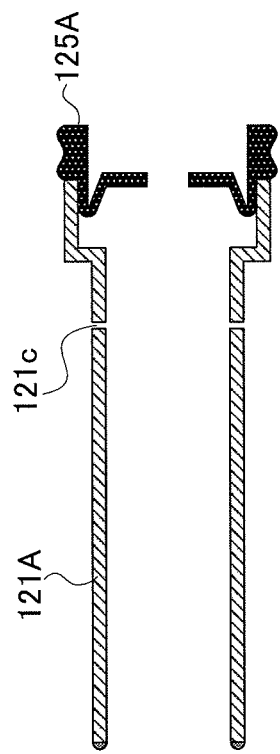
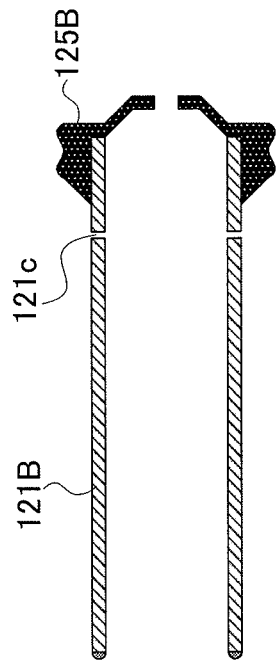
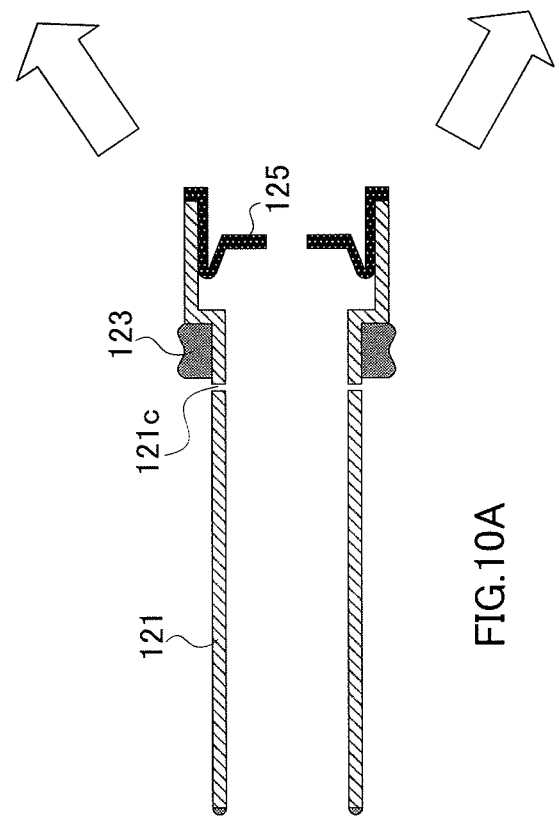

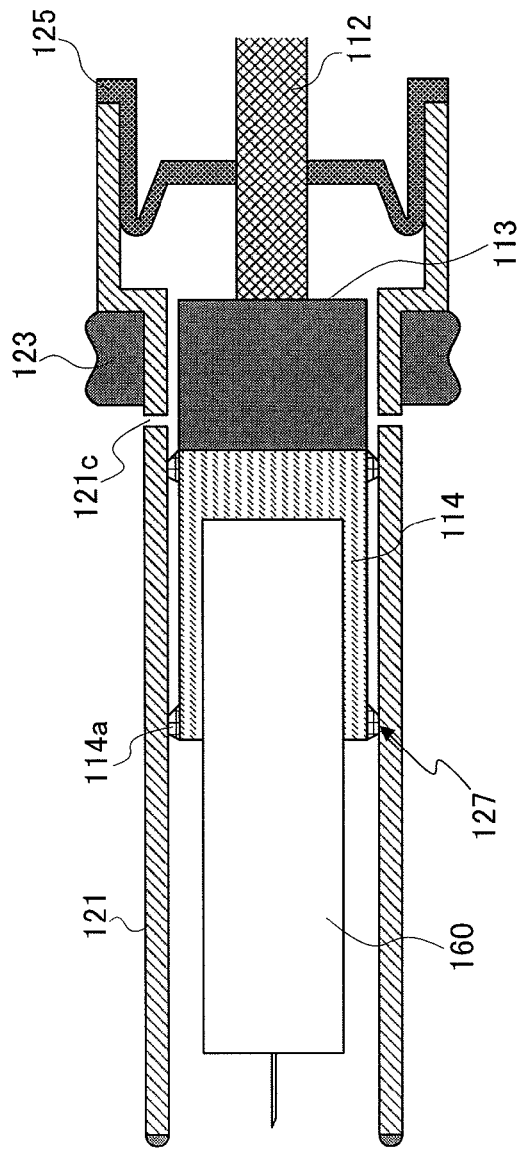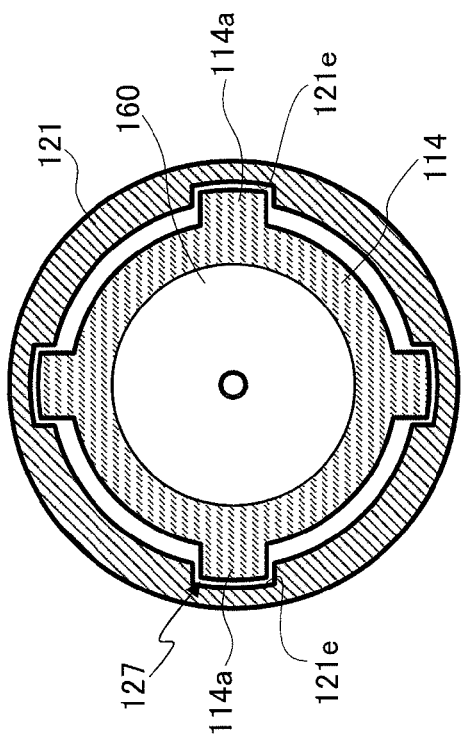
FIG.11A
FIG.11B

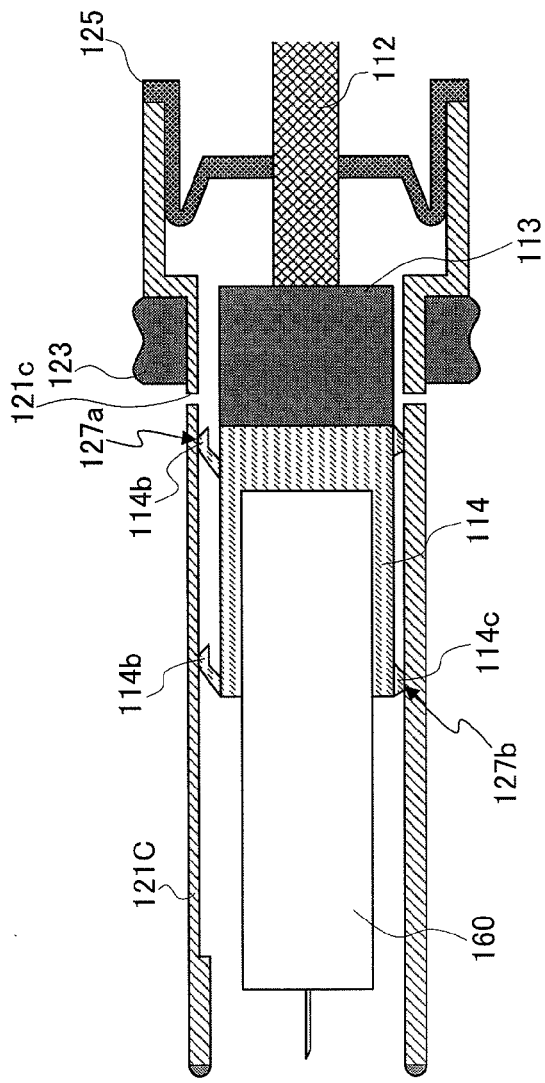
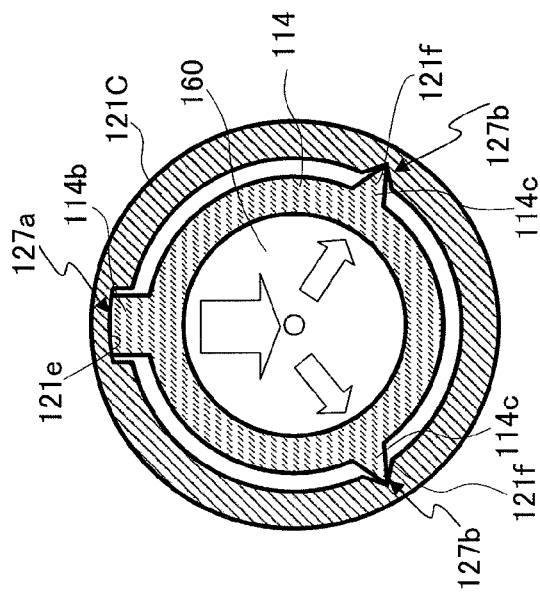
FIG.12A
FIG.12B

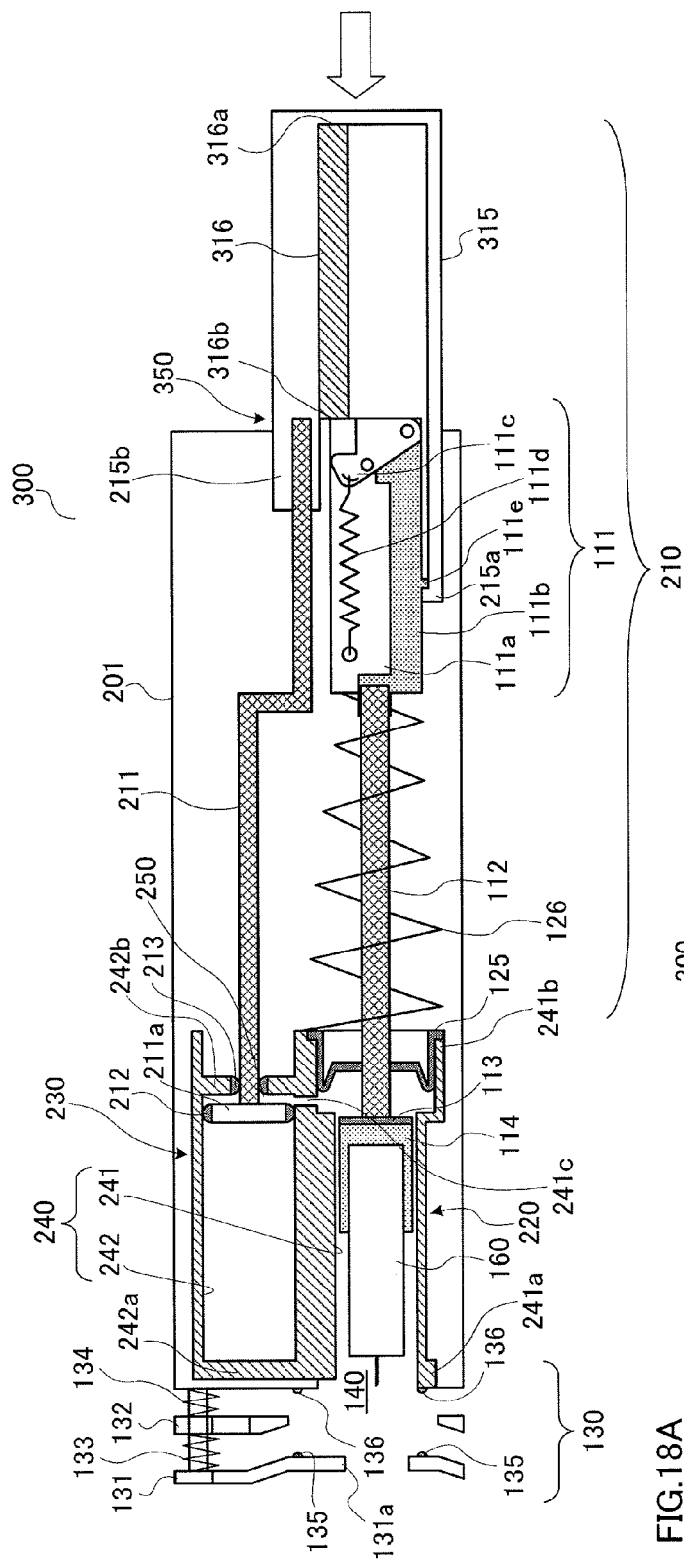
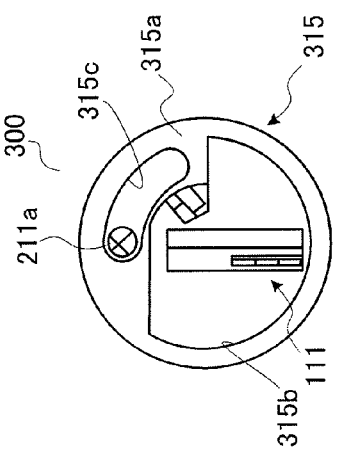
FIG.18A
FIG.18B

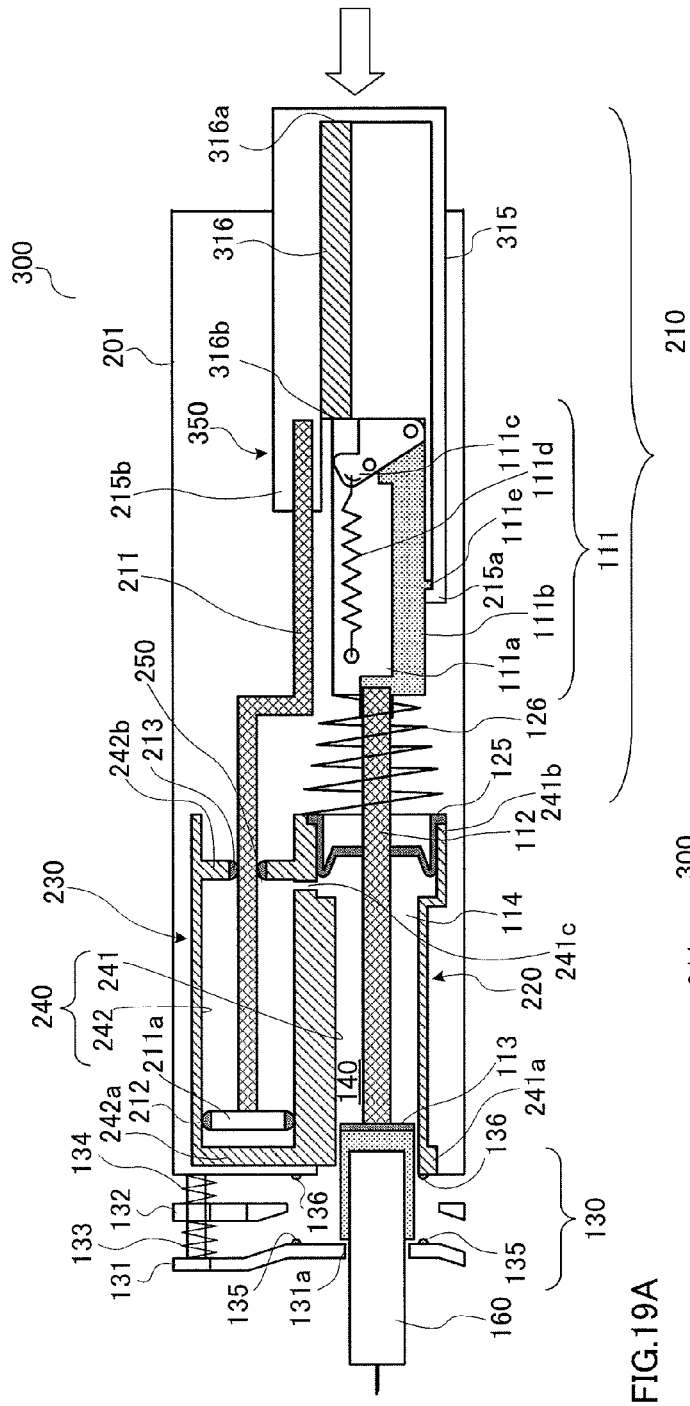
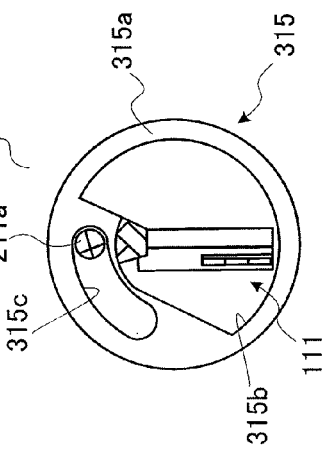
FIG.19A
FIG.19B

PRESSURE REDUCTION MECHANISM, PUNCTURE DEVICE, BLOOD ANALYSIS DEVICE, AND SENSOR MOUNTING MECHANISM

TECHNICAL FIELD

The present invention relates to a decompression mechanism, a puncturing apparatus, blood analysis apparatus and a sensor mounting mechanism used in a puncturing device to sample blood in blood measurement such as blood sugar level measurement.

BACKGROUND ART

Conventionally, various puncturing devices to sample blood from skin of human and animals have been invented for blood analysis, and in recent years, a puncturing device has been invented that accumulates biasing force for puncturing at the same time as a puncturing needle is mounted in the puncturing device (see, for example, Patent Literature 1). This puncturing device performs operation including puncturing and removing, by means of two compression springs, that is, a first compression spring for puncturing and a second compression spring for removing. In addition, a puncturing needle has been developed, in which the part having contacted skin is entirely discarded in order to prevent infection due to adhesion of blood.

Patent Literature 2 discloses a puncturing device including a first biasing means for biasing a puncturing plunger toward the tip and a sucking plunger that has an airtight sealing member and reduces pressure in a housing by moving toward the base end.

Patent literature 3 discloses an apparatus that samples blood from patients in a painless manner, in order to monitor glucose.

FIG. 1 shows a decompression and blood sampling mechanism by means of a spring, used in a conventional puncturing device.

As shown in FIG. 1, decompression and blood sampling mechanism 1 is configured to include piston 2, cylinder 3 that slidably accommodates piston 2, spring 4 that biases to push piston 2 outward, and packing 5 mounted on the outer surface of end part 2a of piston 2.

Packing 5 keeps sealed space 7 airtight, which is formed by bottom surface 2b of end part 2a of piston 2, inner surface 3a of cylinder 3 and skin 6 contacting.

FIG. 1 shows a usual state in which puncturing operation is not performed with the above-described configuration. Now, decompression operation in a puncturing device using decompression and blood sampling mechanism 1 will be described.

First, as shown in FIG. 1B, while spring 4 is compressed in advance, skin 6 contacts inner surface 3a of cylinder 3 to create sealed space 7.

Next, as shown in FIG. 1C, pressing piston 2 is stopped. Then, compressed spring 4 returns to the original state to increase the volume of sealed space 7. By this means, the pressure in sealed space 7 reduces and skin 6 is lifted up, and therefore blood is easily sampled by a puncturing device (not shown) from lifted skin 6.

Next, as shown in FIG. 1D, piston 2 is pressed again to adjust the pressure to the atmospheric pressure, and then skin 6 is removed.

Here, in a case in which the operation shown in FIG. 1D is not performed, when skin 6 is removed when blood is sampled (reduced pressure state: see FIG. 1C), the air rapidly flows in and therefore blood scatters in the puncturing device.

In order to prevent this state, it is necessary to push piston 2 into cylinder 3 again after blood is sampled, as shown in FIG. 1D.

FIG. 2 is a perspective view showing the blood sampling apparatus disclosed in Patent Literature 3. In FIG. 2, the housing of the apparatus is open.

As shown in FIG. 2, blood drawing device 1100 has housing 1102, and housing 1102 has receiving part 1102a and projecting part 1102b. Gasket 1104 seals between receiving part 1102a and projecting part 1102b in housing 1102 and separates receiving part 1102a from projecting part 1102b. Projecting part 1102b is tightly fitted into receiving part 1102a by friction. Projecting elements 1102c and 1102d are used to guide projecting part 1102b to receiving part 1102a. A vacuum pump (not shown), incising assembly 1108, a buttery (not shown) and an electronic device (not shown) are provided in housing 1102. Switch 1109 is provided to activate the electronic device.

During blood sampling, projecting part 1102b is tightly fitted into receiving part 1102a. Receiving part 1102a to contact skin is provided with seal 1110, in housing 1102 of device 1100. Opening 1112 in receiving part 1102a is surrounded by seal 1110. A blood drawing chamber nearby glucose detector 1114 communicates with the surface of skin through opening 1112 in receiving part 1102a. Device 1100 is placed on a region on the surface of skin from which incising assembly 1108 samples blood. In order to sample blood, receiving part 1102a in hosing 1102 of device 1100 is put on skin, and a vacuum is created using seal 1110.

The vacuum pump is operated by pressing switch 1109 to produce sucking action. Skin surrounded by seal 1110 is engorged with blood by sucking action of the vacuum pump. By stretching and lifting skin up to opening 1112, the skin is engorged with blood. After an appropriate period of time usually preset by a programmer who programs electronic devices has passed, incising assembly 1108 is launched to make lancet 1116 penetrate skin which has been lifted up to opening 1112 and engorged with blood. It is preferred to automatically launch lancet 1116 using a solenoid valve (not shown) with a vacuum piston (not shown).

Glucose detector 1114 is inserted in slot 1118 in projecting part 1102b in housing 1102. Receiving part 1102a in housing 1102 moves glucose detector 1114 to a position suitable for testing. The result obtained from glucose detector 1114 is displayed on screen 1120. Receiving part 1102a is separated from projecting part 1102b when lancet 1116 or glucose detector 1114 is replaced. In the process of blood sampling, projecting part 1102b is tightly fitted into receiving section 1102a.

As described above, in device 1100, a sensor (glucose detector 1114) is provided in space in which pressure is reduced. In order to reduce pressure, it is essential that the entire sensor is placed in predetermined space and measured.

CITATION LIST

Patent Literature

PTL 1
Japanese Patent Application Laid-Open No. 2000-245717
PTL 2
Japanese Patent Application Laid-Open No. HEI11-206742
PTL 3
Japanese Patent Application Laid-Open No. 2004-000459

SUMMARY OF INVENTION

Technical Problem

However, a conventional manual decompression and blood sampling apparatus requires manual decompression operation several times, including pushing piston 2 into cylinder 3. This results from that operation is performed several times in order to obtain a reduced pressure space having a large volume and a desired decompression value because a puncturing device is incorporated in the reduced pressure space in the housing of the apparatus.

In addition, these several times of decompression operation is likely to induce timing errors when the reduced pressure is released to return to the atmospheric pressure. If the reduced pressure is not successfully released to return to the atmosphere pressure at an appropriate timing, blood scatters due to rapid air inflow, so that not only the apparatus is contaminated but also it is likely to introduce an infection due to contamination.

In addition, it is very difficult to maintain the apparatus because reduced pressure space is large and operation is complex. If satisfactory maintenance is not performed, not only it is not possible to satisfactorily prevent the above-described adhesion of blood, but also the apparatus is prone to fail. Moreover, troubles and cost increase because maintenance is required frequently.

In view of the above-described problems, it is therefore an object of the present invention to provide a decompression mechanism, a puncturing apparatus, a blood analysis apparatus and a sensor mounting mechanism that can desirably reduce pressure by easy operation, improve operability and provide ease of maintenance.

Solution to Problem

The decompression mechanism according to the present invention adopts a configuration to include: a cylinder having a bottom; a piston having a first end part projecting from the bottom and a second end part that is located in the cylinder and slides along an axis of the cylinder; a first sealing section that seals between the bottom and an outer surface of the piston; a second sealing section that seals between the second end part and an inner surface of the cylinder; and an air chamber that is sealed with the first and second sealing sections and surrounded by the outer surface of the piston and the inner surface of the cylinder, wherein the piston has a connection hole that connects the air chamber with a hollow space opening in the first end part.

The puncturing apparatus according to the present invention adopts a configuration to include: a housing; a puncturing section that is provided in the housing and punctures skin; a puncturing mechanism that operates the puncturing section; a cylinder having a bottom; a piston having a first end part projecting from the bottom and a second end part that is located in the cylinder and slides along an axis of the cylinder; a first sealing section that seals between the bottom and an outer surface of the piston; a second sealing section that seals between the second end part and an inner surface of the cylinder; a third sealing section that is located in a joint between the piston and the puncturing mechanism and seals between a hollow space opening in the first end part and the puncturing mechanism; and an air chamber that is sealed with the first and second sealing sections and surrounded by the outer surface of the piston and the inner surface of the cylinder, wherein the piston has a connection hole that connects the air chamber with the hollow space.

The puncturing apparatus according to the present invention adopts a configuration to include: a housing; a puncturing section that is provided in the housing and punctures skin; and a puncturing mechanism that operates the puncturing section; and a decompression mechanism including: a cylinder having a bottom; a piston that is provided in the cylinder and slides along an axis of the cylinder; a first sealing section that seals between an end part in the piston and an inner surface of the cylinder; a second sealing section that seals an opening in the cylinder and an outer surface of the piston; an air chamber that is sealed with the first and second sealing sections and surrounded by the outer surface of the piston and the inner surface of the cylinder; and a connection hole connecting the air chamber with a space targeted for pressure reduction in the puncturing mechanism.

The blood analysis apparatus according to the present invention that analyzes blood exuding by puncturing using a sensor adopts a configuration to include: a housing; a puncturing section that is provided in the housing and punctures skin; a puncturing mechanism that operates the puncturing section; a cylinder having a bottom; a piston having a first end part projecting from the bottom and a second end part that is provided in the cylinder and slides along an axis of the cylinder; a first sealing section that seals between the bottom and an outer surface of the piston; a second sealing section that seals between the second end part and an inner surface of the cylinder; a third sealing section that is located in a joint between the piston and the puncturing mechanism and seals between a hollow space opening in the first end part and the puncturing mechanism; and an air chamber that is sealed with the first and second sealing sections and surrounded by the outer surface of the piston and the inner surface of the cylinder, wherein: the piston has a connection hole connecting the air chamber with the hollow space; and the first end part has a contacting part that can contact skin and a holding part that holds a sensor.

The blood analysis apparatus according to the present invention that analyzes blood exuding by puncturing using a sensor adopts a configuration to include: a housing; a puncturing section that is provided in the housing and punctures skin; a puncturing mechanism that operates the puncturing section; and a decompression mechanism including: a cylinder having a bottom; a piston that is provided in the cylinder and slides along an axis of the cylinder; a first sealing section that seals between an end part of the piston and an inner surface of the cylinder; a second sealing section that seals an opening in the cylinder and an outer surface of the piston; an air chamber that is sealed with the first and second sealing sections and surrounded by the outer surface of the piston and the inner surface of the cylinder; and a connection hole connecting the air chamber and space targeted for pressure reduction in the puncturing mechanism.

The blood analysis apparatus according to the present invention including a housing, a sensor having an opening and a puncturing section that is accommodated in the housing and punctures skin with a puncturing needle or laser light. The blood analysis apparatus analyzes blood by passing the puncturing needle or laser light through the opening to puncture skin and introduces blood exuding from the skin by puncturing into the sensor. The blood analysis apparatus adopts a configuration to include: a supporting section that slidably projects from a housing edge, which is one end of the housing; a sensor holding part that is slidably supported by the support part and holds the sensor; a skin contacting part that is provided on a tip of the support part and can contact skin; a first spring that biases to keep a predetermined distance between the sensor holding part slidably supported by the support part and the skin contacting part with a first stretching strength; a second spring that biases to keep a predetermined distance between the sensor holding part slidably supported by the support part and the housing edge with a second stretching strength; a first sealing section that seals between the opening in the sensor held by the sensor holding part and the skin contacting part when the skin contacting part is pushed toward the housing edge; and the second sealing section that seals the opening in the sensor held by the sensor holding part and the housing edge when the skin contacting part is pushed toward the housing edge.

The sensor mounting mechanism according to the present invention adopts a configuration to include: a support part slidably projecting from a housing edge; a sensor holding part that is slidably supported by the support part and holds a sensor; a skin contacting part that is provided on a tip of the support part and can contact skin; a first spring that biases to keep a predetermined distance between the sensor holding part slidably supported by the support part and the skin contacting part with a first stretching strength; a second spring that biases to keep a predetermined distance between the sensor holding part slidably supported by the support part and the housing edge with a second stretching strength; a first sealing section that seals between the sensor held by the sensor holding part and the skin contacting part when the skin contacting part is pushed toward the housing edge; and a second sealing section that seals between the sensor held by the sensor holding part and the housing edge when the skin contacting part is pushed toward the housing edge.

Advantageous Effects of Invention

According to the present invention, airtightness between a decompression and blood sampling mechanism and a puncturing operation activating mechanism is maintained, so that it is possible to reduce pressure only by pushing a skin contacting part to the apparatus body side.

In addition, air pressure adjustment to make pressure similar to the atmosphere pressure is performed in a series of operation, so that it is possible to adequately separate skin from the apparatus, and therefore it is possible to prevent blood from scattering due to rapid air inflow.

Moreover, at the time of puncturing, a sensor holding part, a skin contacting part and a housing edge are sealed through first and second sealing sections, so that it is possible to desirably reduce pressure, improve operability and provide ease of maintenance.

BRIEF DESCRIPTION OF DRAWINGS

FIGS. 3A, B and C each show the principle of a decompression and blood sampling mechanism according to the present invention;

FIGS. 3D, E and F each show the principle of a decompression and blood sampling mechanism according to the present invention;

FIG. 4 is a cross sectional view showing a configuration of a laser puncturing device having the decompression and blood sampling mechanism according to the present invention;

FIGS. 8A, B, C and D each explain puncturing operation of a needle puncturing device according to Embodiment 1;

FIGS. 8E, F, G, H and I each explain puncturing operation of a needle puncturing device according to Embodiment 1;

FIG. 10 shows a configuration example of the packing configuration of a piston in a puncturing device according to Embodiment 1;

FIG. 11 shows an anti-shake puncturing needle guide attached to the piston in the puncturing device according to Embodiment 1;

FIG. 12 shows the anti-shake puncturing needle guide attached to the piston in the puncturing device according to Embodiment 1;

FIGS. 18A and B each show a puncturing device according to Embodiment 3 of the present invention;

FIGS. 19A and B each show mounting and removing operation of the puncturing device according to Embodiment 3;

DESCRIPTION OF EMBODIMENTS

Figure 1:
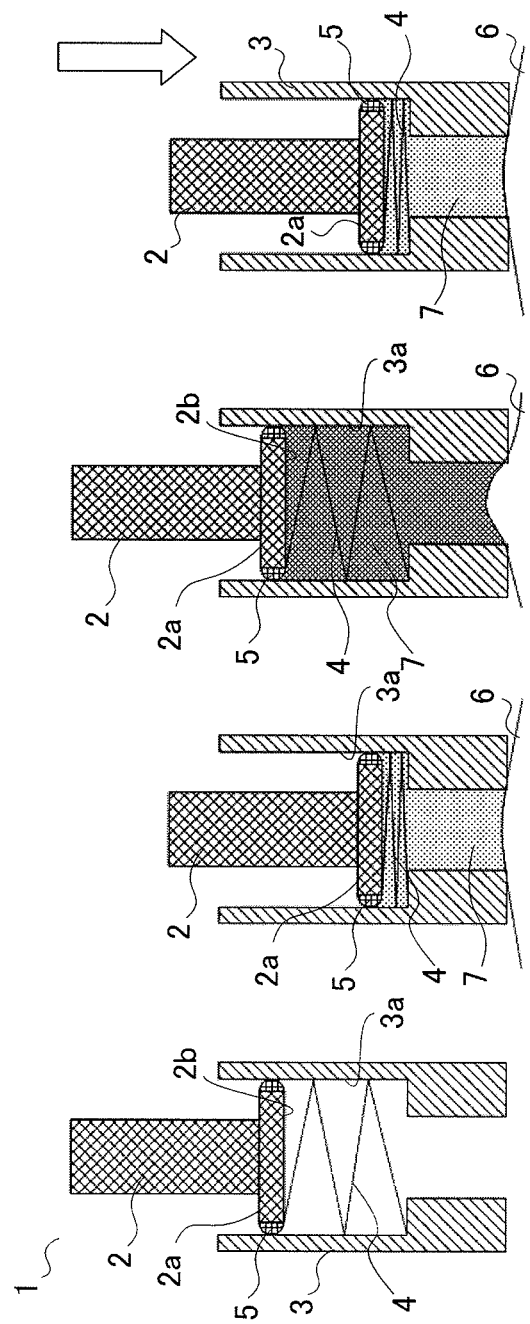
FIG. 1 shows a decompression and blood sampling mechanism by spring used in a conventional puncturing device.
Figure 2:
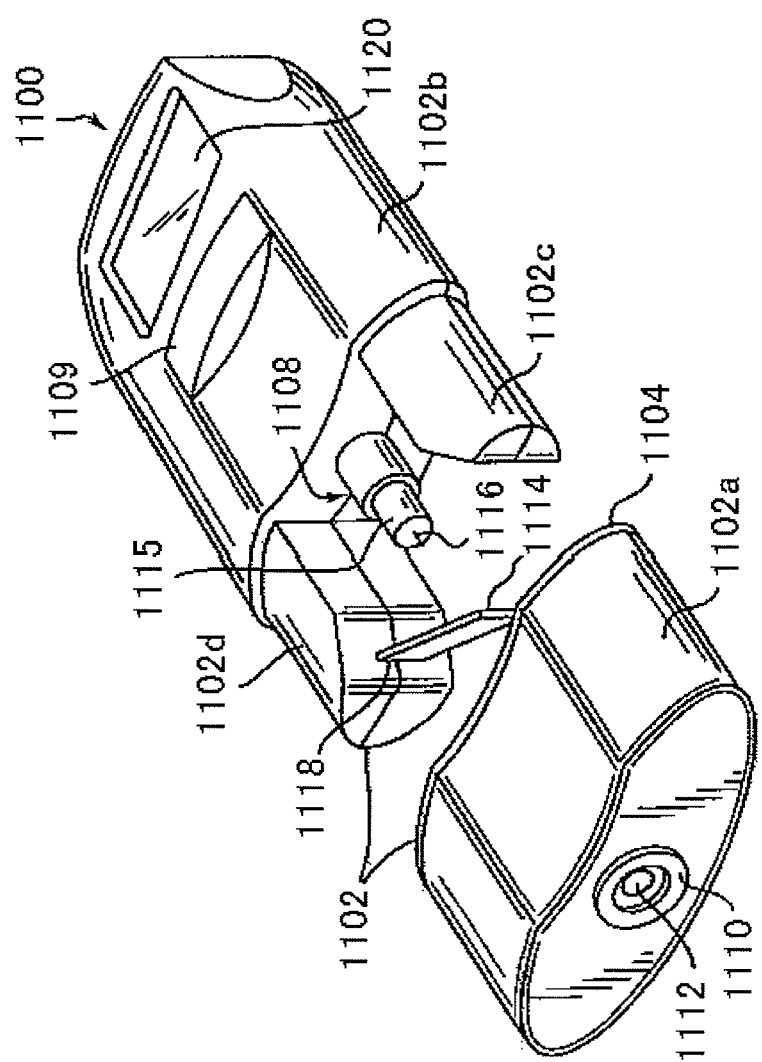
FIG. 2 is a perspective view showing a conventional blood sampling apparatus.

Now, embodiments of the present invention will be described in detail with reference to the accompanying drawings.

(Explanation of the Principle)

First, the principle of a decompression and blood sampling mechanism according to the present invention will be explained.

FIG. 3A, FIG. 3B, FIG. 3C, FIG. 3D, FIG. 3E and FIG. 3F (hereinafter, collectively refer to as FIG. 3) each explain the principle of the decompression and blood sampling mechanism according to the present invention.

As shown in FIG. 3, decompression and blood sampling mechanism 10 is configured to include: piston 11 having skin contacting part 11a to contact skin in one end and end part 11b in the other end; cylinder 12 that has opening part 12a to allow piston 11 pass through, projects skin contacting part 11a in piston 11 from opening part 12a and slidably accommodates end part 11b in piston 11 inside; packing 13 attached to the outer surface of end part 11b in piston 11; and packing 14 attached to the inner surface of opening part 12a in cylinder 12.

Piston 11 has connection hole 11d that connects cylindrical internal space 16 with sealed space 17 formed by inner surface 12b of cylinder 12 that faces opening part 12a, bottom surface 11c of end part 11b in piston 11 and the outer surface of piston 11. Connection hole 11d is open in a position to connect to sealed space 17 always sealed with packing 13 and packing 14 regardless of sliding states of piston 11. Therefore, connection hole 11d is open nearby end part 11b in piston 11. It is preferable to open a plurality of connection holes 11d.

Packing 13 and packing 14 maintain airtightness of sealed space 17. In addition, when skin 18 contacts skin contacting part 11a in piston 11, packing 13 and packing 14 maintain airtightness between cylindrical internal space 16 closed by contacting skin 18 and sealed space 17 connecting to this cylindrical internal space 16 via connection hole 11d.

In addition, as shown in FIG. 3F, it is preferable to provide spring 15 that biases piston 11 to return to the original state at all times.

In this way, decompression and blood sampling mechanism 10 has cylinder 12 having opening part 12a; piston 11 in cylinder 12 having skin contacting part 11a projecting from opening 12a and end part 11b sliding along the axis of cylinder 12; packing 14 that seals between opening part 12a and the outer surface of piston 11; packing 13 that seals between end part 11b and the inner surface of cylinder 12; and sealed space 17 surrounded by packing 13, packing 14, the outer surface of piston 11 and the inner surface of cylinder 12. Piston 11 has connection hole 11d to connect sealed space 17 and cylindrical internal space 16 opening in skin connecting part 11a.

FIG. 3A shows a usual state in which puncturing operation is not performed (initial state) with the above-described configuration. Now, operation to reduce pressure in a puncturing device using decompression and blood sampling mechanism 10.

As shown in FIG. 3B, when puncturing is attempted, skin 18 is approached by the entire decompression and blood sampling mechanism 10 to contact skin contacting part 11a in piston 11. The bottom of cylindrical internal space 16 in piston 11 is open in the initial state (the state shown in FIG. 3A), and then, becomes initial sealed space 1 for the following reason. That is, skin contacting part 11a contacts skin 18, so that cylindrical internal space 16 becomes sealed space 16A, and piston 11 is pushed toward skin 18, and therefore sealed space 17 sealed with packing 13 and packing 14 is expanded to create a negative pressure. This negative pressure passes through connection hole 11d to reduce the pressure in sealed space 16A. That is, piston 11 is pushed up into cylinder 12 (see the arrow indicating the upward direction in FIG. 3B), so that the volume of sealed space 17 increases and the pressure in sealed space 16A connecting to sealed space 17 is reduced.

FIG. 3C shows a state in which piston 11 is pushed up into cylinder 12 more deeply and the pressure in sealed space 17 and sealed space 16A is further reduced. In this state, force of piston 11 to return to its original state acts on.

FIG. 3D shows the same state as in FIG. 3C and shows the force of piston 11 to return to the original state (see the arrows indicating the downward direction in FIG. 3D).

As shown in FIG. 3E, when the force to push up piston 11 is reduced, the force to return from the negative pressure state to the atmosphere pressure state acts on as described above, and therefore piston 11 returns to the original state and skin contacting part 11a in piston 11 separates from skin 18 when the pressure is around the atmosphere pressure.

Here, the relationship between skin and the adhesion of the skin contacting part is as follows. That is, when a decompression value is greater, pushing force increases and also adhesion increases, but the adhesion is small at the point skin separates from the skin contacting part. As a result of this, due to the relationship in the sliding friction and the leakage of air between piston 11 and cylinder 12, it is difficult to completely return piston 11 to the original state. Therefore, as shown in FIG. 3F, it is preferable to provide spring 15 in cylinder 12 to offset piston 11 to return to the original state at all times. This spring 15 provides an effect of improving the adhesion between skin 18 and skin contacting part 11a at the time in early pressure reduction.

In this way, it is possible to realize a decompression mechanism only by pushing skin contacting part 11a in piston 11 to the apparatus body side.

Particularly, decompression and blood sampling mechanism 10 according to the present invention reduces pressure and samples blood only by pushing the part having been punctured against piston 11 and pushing piston 11 toward the apparatus body side, and, when the required amount of blood is obtained, air pressure adjustment to make the pressure similar to the atmosphere pressure is performed by weakening the pushing force to separate skin 18 from the apparatus in a series of operation, and therefore blood does not scatter due to rapid air inflow.

It is possible to apply decompression and blood sampling mechanism 10 according to the above-described principle, to a puncturing apparatus having any puncturing means.

Hereinafter, a puncturing device having a laser puncturing means will be shown in FIG. 4 and FIG. 5, and a puncturing device having a needle puncturing means will be shown in FIG. 6.

FIG. 4A and FIG. 4B (hereinafter, collectively referred to as FIG. 4) are cross sectional views each showing a configuration of a laser puncturing device having decompression and blood sampling mechanism 10A. The same components as in FIG. 3 are assigned the same reference numerals, and overlapping descriptions will be omitted.

As shown in FIG. 4, laser puncturing device 20 has laser puncturing apparatus 21 that punctures skin with laser light without contacting and decompression and blood sampling mechanism 10A.

Decompression and blood sampling mechanism 10A is the same as decompression and blood sampling mechanism 10 except for the configuration of end part 11b in piston 11.

Piston 11 in decompression and blood sampling mechanism 10A is provided with laser light passing member 11e at the center of end part 11b that allows laser light from laser puncturing apparatus 21 to pass through.

As shown in FIG. 4A, when puncturing is attempted, skin 18 is approached by the entire decompression and blood sampling mechanism 10A to contact skin contacting part 11a in piston 11.

As shown in FIG. 4B, piston 11 contacting skin 18 is pushed up into cylinder 12 to reduce the pressure in sealed space 17 and sealed space 16A. The pressure in sealed space 16A is reduced to lift up skin 18, and therefore puncturing is easily performed. Laser light emitted from laser puncturing apparatus 21 passes through laser light passing member 11e, passes through sealed space 16A and arrives at skin 18, and then, puncturing is accomplished.

Figure 5A:
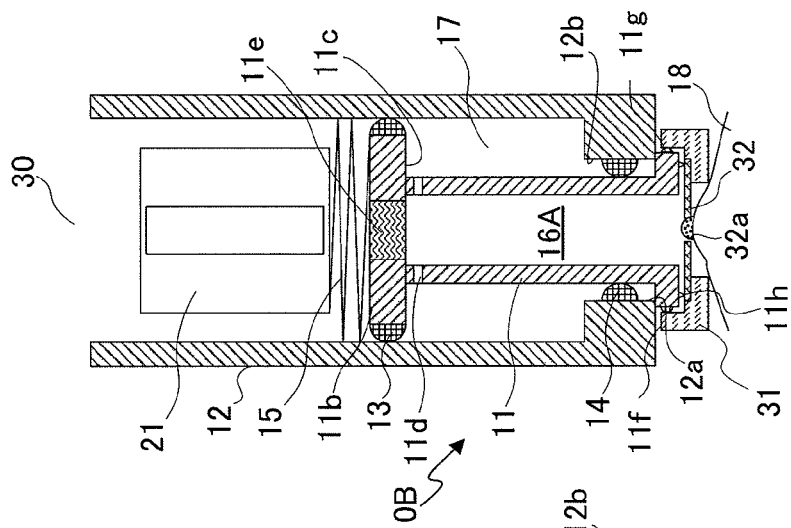
FIG. 5 is a cross sectional view showing a configuration of a puncturing and blood sampling apparatus having the decompression and blood sampling mechanism according to the present invention.
Figure 5B:
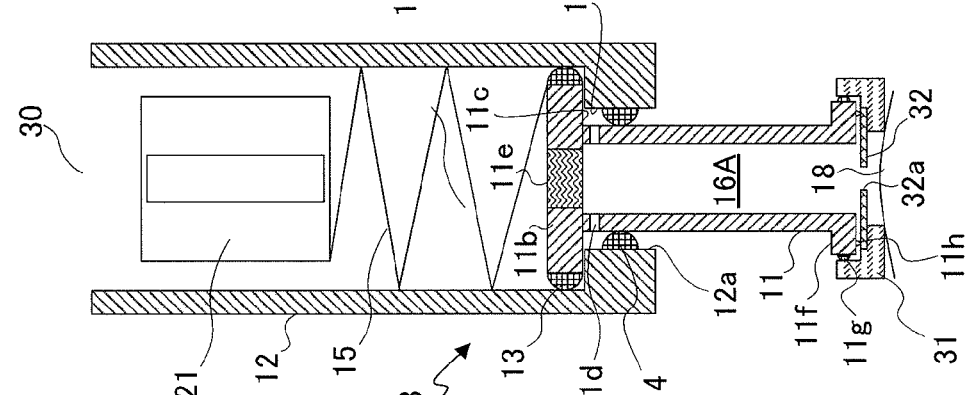
Figure 5C:
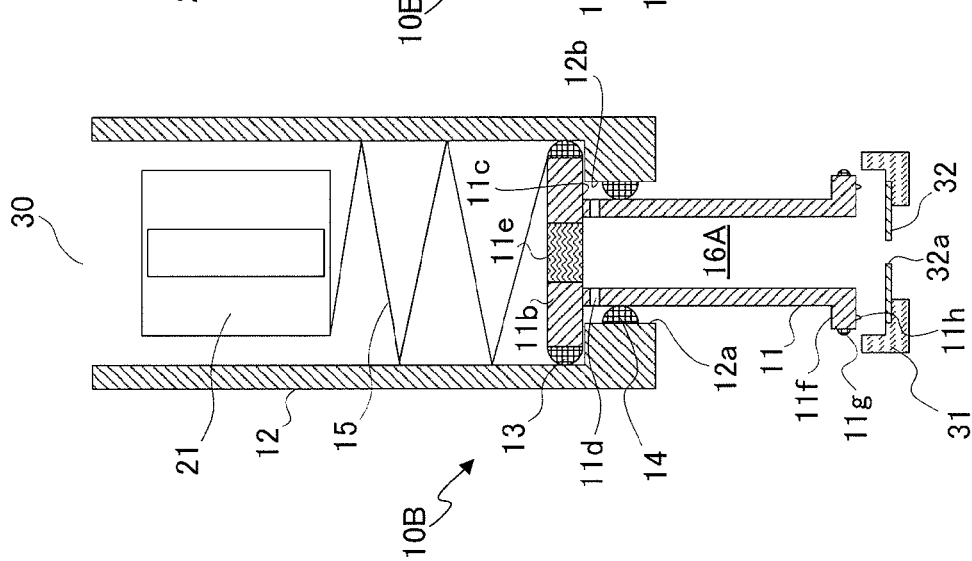

FIG. 5A, FIG. 5B and FIG. 5C (hereinafter collectively referred to as FIG. 5) are cross sectional views each showing a configuration of a puncturing and blood sampling apparatus having decompression and blood sampling mechanism 10B. The same components as in FIG. 3 and FIG. 4 are assigned the same reference numerals, and overlapping descriptions will be omitted.

As shown in FIG. 5, laser puncturing device 30 has laser puncturing apparatus 21 that punctures skin with laser light without contacting, decompression and blood sampling mechanism 10B and holder 31 that holds a blood sensor (hereinafter "sensor").

Decompression and blood sampling mechanism 10B is the same as decompression and blood sampling mechanism 10A shown in FIG. 4 except for the configuration of skin contacting part 11a in piston 11.

Piston 11 in decompression and blood sampling mechanism 10B has holder mounting part 11f, instead of skin contacting part 11a in piston 11 shown in FIG. 3. Holder mounting part 11f is provided with packing 11g in the outer surface and holding claw 11h in the bottom surface facing holder 31.

Holder 31 and holder mounting part 11f sandwich and hold sensor 32 placed on holder 31.

Decompression operation of decompression and blood sampling mechanism 10B is the same as in FIG. 3 and FIG. 4, so that descriptions will be omitted.

Laser light emitted from laser puncturing apparatus 21 passes through opening 32a in sensor 32 and arrives at skin 18.

Part of the surface of skin 18 is evaporated with laser light, and therefore blood exuding from the surface of skin 18 flows into sensor 32 through opening 32a. Reagent (not shown) (for example, reagent used to measure blood sugar levels, lactate values and cholesterol levels) is placed in sensor 32. Upon arriving at blood analysis reagent, blood reacts on the reagent, so that it is possible to know the result of the analysis.

Sensor 32 may be integrated with the holder, or used by itself. Here, a configuration in which sensor 32 is used by itself, will be described later with an embodiment.

Figure 6:
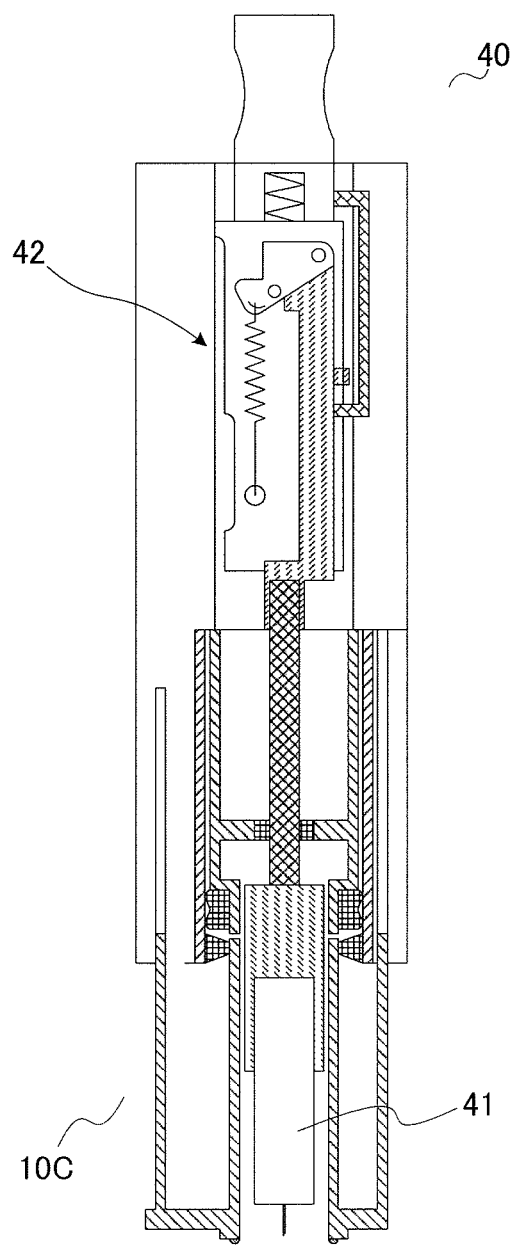
FIG. 6 is a cross sectional view showing a configuration of a needle puncturing device having the decompression and blood sampling mechanism according to the present invention.

FIG. 6 is a cross sectional view showing a configuration of a needle puncturing device having decompression and blood sampling mechanism 10C. The same components as in FIG. 3 are assigned the same reference numerals, and overlapping descriptions will be omitted.

As shown in FIG. 6, needle puncturing device 40 has puncturing needle 41, mechanism section 42 that ejects and retracts puncturing needle 41 and decompression and blood sampling mechanism 10C.

Decompression and blood sampling mechanism 10C operates according to the same principle as of decompression and blood sampling mechanism 10 shown in FIG. 3. Decompression and blood sampling mechanism 10C holds puncturing needle 41 in reduced pressure space (equivalent to reduced pressure space 16A shown in FIG. 3).

Mechanism section 42 is placed outside the above-described reduced pressure space and makes puncturing needle 41 perform puncturing.

Here, the detailed configuration of needle puncturing device 40 will be explained with the following embodiment.

(Embodiment 1)

With Embodiments 1 to 4, "decompression and blood sampling mechanism" will be explained.

Figure 7:
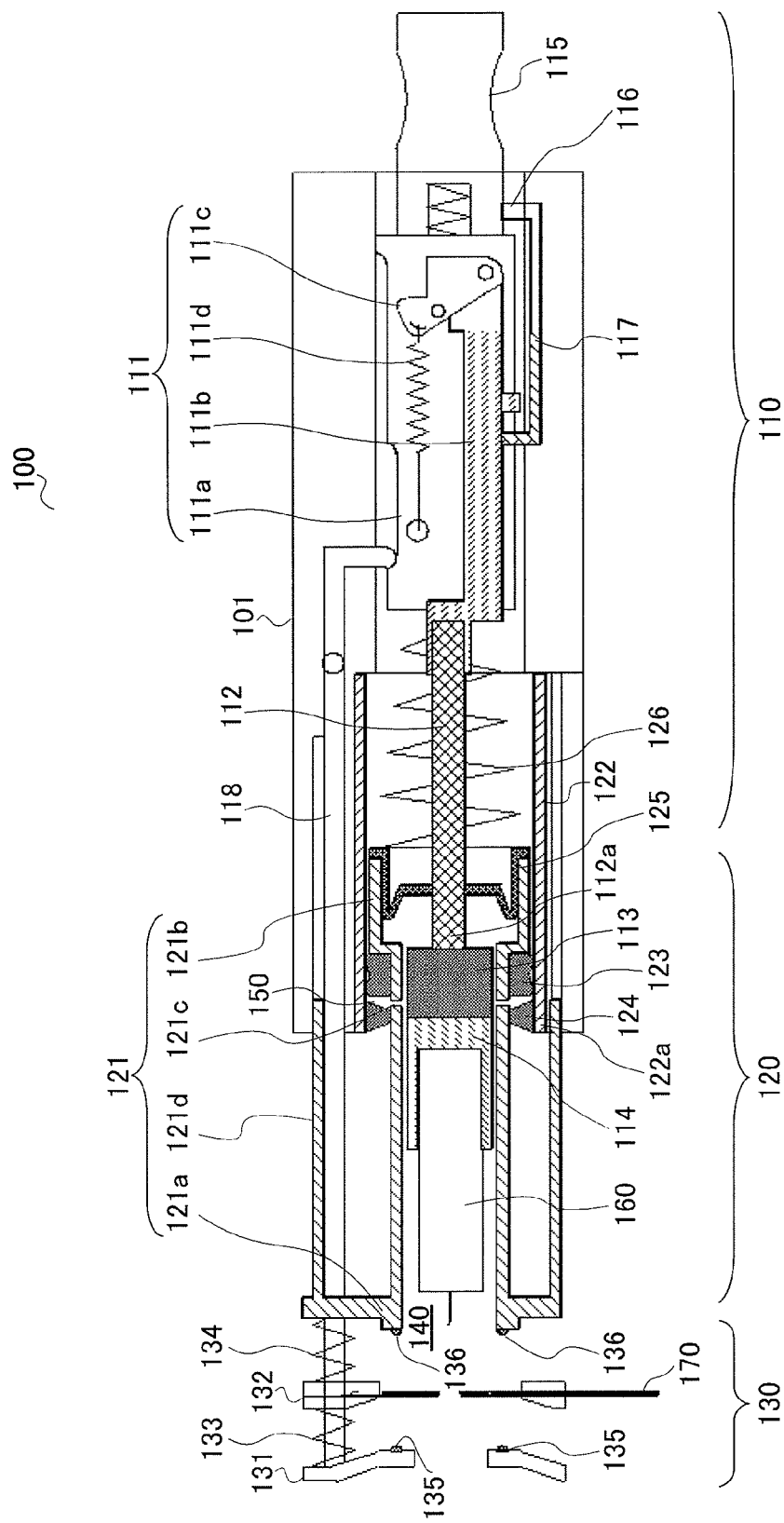
FIG. 7 is a cross sectional view showing a puncturing device according to Embodiment 1 of the present invention.

FIG. 7 is a cross sectional view showing a puncturing device based on the above-described basic principle, according to Embodiment 1 of the present invention. The present embodiment is an example in which a decompression and blood sampling mechanism based on the above-described basic principle is applied to a needle puncturing device.

As shown in FIG. 7, needle puncturing device 100 is configured to mainly include: housing 101; puncturing operation activating mechanism 110 (equivalent to mechanism section 42 shown in FIG. 6) that is provided in housing 101 and located outside the decompression and blood sampling mechanism to allow puncturing needle 160 (equivalent to puncturing needle 41 shown in FIG. 6) to perform puncturing; decompression and blood sampling mechanism 120 (equivalent to decompression and blood sampling mechanism 10C shown in FIG. 6) that holds sensor 170 and reduces the pressure in the space formed by contacting skin; and sensor mounting mechanism 130.

First, puncturing operation activating mechanism 110 will be explained.

Puncturing operation activating mechanism 110 is placed out of decompression and blood sampling mechanism 120, and has lancet section 111 that allows puncturing needle 160 to perform puncturing operation and rod 112 that transfers puncturing operation of lancet section 111 to puncturing needle 160. Lancet section 111 has base plate 111a to which plunger 111b, lever 111c, and pull spring 111d are attached. Rod 112 is connected to plunger 111b, and can slide in a predetermined range in piston 121 in decompression and blood sampling mechanism 120 described later, in conjunction with operation of plunger 111b. Plunger 111b returns to the natural state by rotation of lever 111c biased by pull spring 111d.

In addition, puncturing operation activating mechanism 110 is placed in decompression and blood sampling mechanism 120, and has packing 113 provided in end part 112a of rod 112 and puncturing needle holder 114 attached to packing 113 to mount puncturing needle 160.

In addition, puncturing operation activating mechanism 110 has eject knob 115 also used as a puncturing depth adjusting section. After finishing puncturing operation, eject knob 115 is pushed. By this means, an eject rod (not shown) biased by an eject rode spring (not shown) pushes puncturing needle holder 114 forward in housing 101, and therefore, it is possible to remove puncturing needle holder 114 from the puncturing device without touching a puncturing needle by hand. Meanwhile, when a puncturing depth is adjusted, eject knob 115 is rotated. Eject knob 115 has a spiral groove (not shown) and protrusion 116 fitted into this spiral groove, where protrusion 116 is connected to lock plate 117. In the above-described puncturing depth adjustment, the position of protrusion 116 in the axial direction is changed by rotating eject knob 115, and therefore it is possible to move the position of lock plate 117 forward and backward in housing 101.

Here, lancet section 111 and cylinder 122 in decompression and blood sampling mechanism 120 described later, are connected through rod 118.

Next, decompression and blood sampling mechanism 120 will be explained.

Decompression and blood sampling mechanism 120 is a decompression mechanism based on the same basic principle as of decompression and blood sampling mechanisms 10, 10A to 10C described with reference to FIG. 3 to FIG. 6. Here, although the basic principle is the same, the detailed configuration is different between them, from the viewpoint of implementation. With the present embodiment shown in FIG. 7, the main different point is that puncturing operation activating mechanism 110 allows a puncturing needle to perform puncturing in piston 121 in decompression and blood sampling mechanism 120. Now, detailed descriptions will be explained.

Decompression and blood sampling mechanism 120 has a configuration to include: piston 121 having one end part 121a forming part of sensor mounting mechanism 130 and the other end part 121b slidably supporting rod 112 in lancet section 111; cylinder 122 that has opening 122a to allow piston 121 to pass through, projects end part 121a in piston 121 from opening 122a and slidably accommodates end part 121b in piston 121 inside; packing 123 attached to the outer surface of end part 121b in piston 121; packing 124 attached to the inner surface of opening 122a in cylinder 122; packing 125 attached to the inner surface of end part 121b in piston 121 to maintain airtightness around rod 112; and spring 126 that biases to return piston 121 to the original position at all times.

Piston 121 has a cylindrical shape and includes internal space 140 inside the cylindrical shape body. Puncturing needle holder 114 in which puncturing needle 160 is mounted, and packing 113 slidably moves in this cylindrical internal space 140 following puncturing operation of rod 112.

Piston 121 has connection hole 121c that connects the above-described cylindrical internal space 140 with sealed space (hereinafter "reduced pressure chamber") 150 formed by packing 123 attached to the outer surface of piston 121 and packing 124 attached to opening 122a in cylinder 122. Connection hole 121c is open in the position to connect to decompression chamber 150 always sealed with packing 123 and packing 124 regardless of sliding states of piston 121. Therefore, connection hole 121c is open between packing 123 and packing 124 in the natural state. It is preferable to open a plurality of connection holes 121c. The outer surface of end part 121a in piston 121 is folded to return to housing 101 to form insertion part 121d. Insertion part 121d is slidably inserted in limiting section 101a (not shown) that is open in housing 101. The entire outer surface of end part 121a in piston 121 serves as a guide, which is insertion part 121d inserted in limiting section 101a in housing 101, so that it is possible to prevent piston 121 from being wobbling at the time of puncturing and so forth.

Packing 123 and packing 124 maintain airtightness of reduced pressure chamber 150. When skin contacts skin contacting part 131 in sensor mounting mechanism 130, packing 123 and packing 124 maintain the airtightness of cylindrical internal space 140 closed by contacting skin and reduced pressure chamber 150 connecting to this cylindrical internal space 140 via connection hole 121c.

Packing 125 tightly adheres to packing 113 at the time of pressure reduction to more securely maintain the reduced pressure state.

Next, sensor mounting mechanism 130 will be explained.

Sensor mounting mechanism 130 has a configuration to include: skin contacting part 131; sensor holding part 132 to hold sensor 170 in a predetermined position; end part 121a in piston 121, which is the main part of sensor mounting mechanism 130; first spring 133 that biases between skin contacting part 131 and sensor holding part 132 at a first stretching strength; second spring 134 that biases between sensor holding part 132 and end part 121a at a second stretching strength; first packing 135 that seals between skin contacting part 131 and sensor 170 at the time of puncturing; second packing 136 that seals between end part 121a and sensor 170 at the time of puncturing; and movable holding support 137 (shown in FIG. 21A described later) that movably holds skin contacting part 131, sensor holding part 132 and end part 121a.

Sensor mounting mechanism 130 sandwiches and holds sensor 170 placed on holder 132 between the inner surface of skin contacting part 131 and end part 121a in piston 121. In addition, in this state, first packing 135 and second packing 136 adhere to sensor 170 to close the gap between sensor 170 and skin contacting part 131 and the gap between sensor 170 and end part 121a.

Here, with Embodiment 1, "decompression and blood sampling mechanism" will be explained. Sensor mounting mechanism 130 will be explained again with Embodiment 5 described later, with reference to FIG. 7.

Now, puncturing operation of needle puncturing device 100 having the above-described configuration will be explained.

First, basic puncturing operation will be explained.

FIG. 8A, FIG. 8B, FIG. 8C, FIG. 8D, FIG. 8E, FIG. 8F, FIG. 8G, FIG. 8H and FIG. 8I (hereinafter collectively referred to as FIG. 8) each explain puncturing operation of needle puncturing device 100.

FIG. 8A shows a state in which only puncturing needle 160 is mounted (this state is referred to as "initial state").

As shown in FIG. 8B, sensor 170 is mounted in sensor mounting mechanism 130.

Next, as shown in FIG. 8C, lancet section 111 in puncturing operation activating mechanism 110 is drawn into housing 101 (puncturing needle 160 is moved upward in FIG. 8C) and charged to allow puncturing. To be more specific, pull spring 111d in lancet section 111 is charged to adhere packing 113 to packing 125.

As shown in FIG. 8D, skin 180 of a finger (or palm, upper arm) is pushed to skin contacting part 131 in sensor mounting mechanism 130 to secure the airtightness of cylindrical internal space 140 in piston 121. By this means, it is possible to secure the airtightness in decompression chamber 150 connecting skin contacting part 131 through connection hole 121c.

After that, while pushing skin 180 to skin contacting part 131, skin contacting part 131 is continuously pushed (moved forward in FIG. 8D), so that the pressure in decompression chamber 150 is reduced as shown in hatching in FIG. 8E. At the time of pressure reduction, packing 125 tries to sink into decompression chamber 150, but fixed to packing 113, and therefore tightly adhere to packing 113.

FIG. 8F shows a state in which puncturing has been performed. At the time of puncturing, packing 125 sinks into decompression chamber 150 and moves puncturing needle 160 by this sinking force. Puncturing needle 160 further projects by inertia. Here, it is possible to adjust the length of puncturing needle 160 projecting with a depth adjustment mechanism by rotating eject knob 115 as described above.

After puncturing needle 160 punctures skin 180, blood exuding from the surface of skin 180 is introduced into sensor 170 as shown in FIG. 8G, and then measurement starts. In addition, a cam mechanism (not shown) in lancet section 111 returns puncturing needle 160 to the position before charging.

As shown in FIG. 8H, after finishing measurement, skin 180 pushed onto skin contacting part 131 is returned (moved downward in FIG. 8H), and therefore the pressure in decompression chamber 150 returns to the atmosphere pressure.

As shown in FIG. 8I, a finger (or palm, upper arm) separates from skin contacting part 131, so that puncturing and blood sampling are completed. Then, sensor 170 is discharged.

Next, decompression operation of decompression and blood sampling mechanism 120 will be described in detail.

FIG. 9A, FIG. 9B, FIG. 9C, FIG. 9D, FIG. 9E and FIG. 9F (hereinafter collectively referred to as FIG. 9) each explain decompression operation of decompression and blood sampling mechanism 120.

Figure 9A:
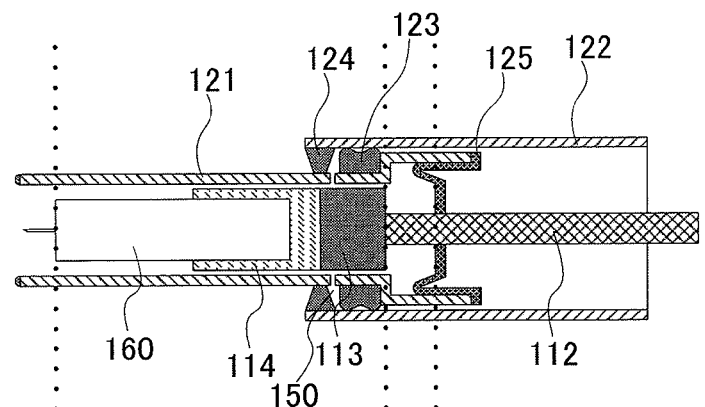
FIGS. 9A, B and C each explain decompression operation of the decompression and blood sampling mechanism according to Embodiment 1.

FIG. 9A shows a usual state (initial state).

Figure 9B:
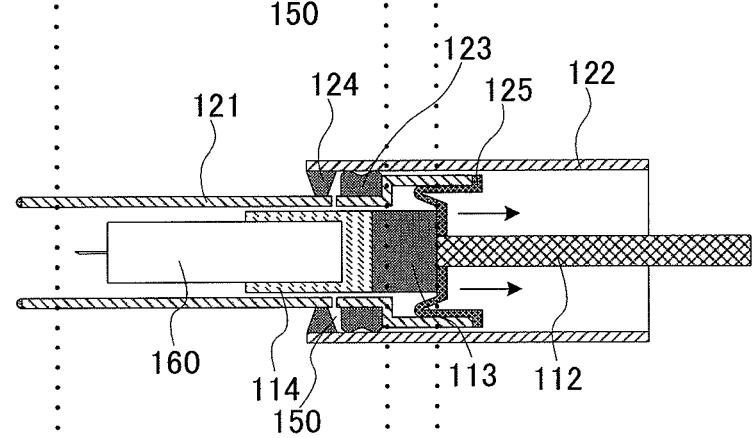
FIGS. 9D, E and F each explain decompression operation of the decompression and blood sampling mechanism according to Embodiment 1.

FIG. 9B shows a puncturing stand-by state, where puncturing needle 160 is charged in needle puncturing device 100 to allow puncturing needle 160 to perform puncturing, and packing 113 fixed to puncturing needle holder 114 adheres to packing 125. More preferably, packing 113 is pushed into packing 125 to the extent that packing 125 slightly distorts. This effect early in pressure reduction is as follows.

If packing 125 does not distort, the airtightness in decompression chamber 150 is maintained only by rod 112 and packing 125.

As shown by the arrows in FIG. 9B (pointing to the right in FIG. 9B), when packing 125 distorts, it is possible to reduce the adhesion between rod 112 and packing 113 by adhesion between packing 125 adhering to the inner wall of decompression chamber 150 and packing 113, in addition to the above-described adhesion, and therefore it is possible to easily slide rod 112.

Figure 9C:
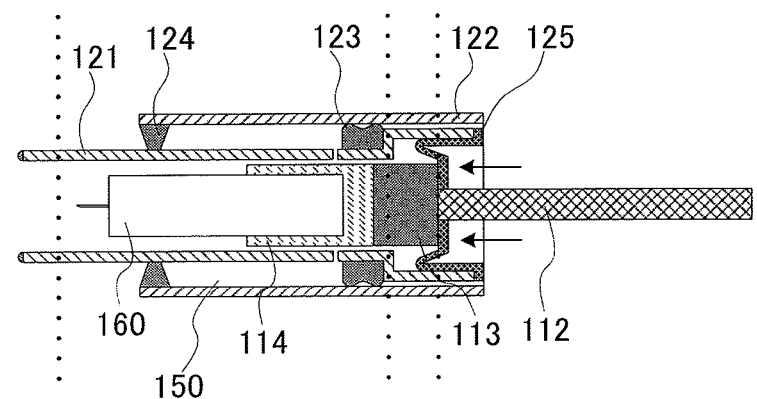

FIG. 9C shows a state in which the pressure in cylinders 121 and 122 are reduced. As shown by the arrows in FIG. 9C (pointing to the left in FIG. 9C), force to push packing 125 into decompression chamber 150 generates. This force allows packing 125 to more tightly adhere to packing 113 fixed to puncturing needle holder 114 to prevent air from entering decompression chamber 150. In this case, the airtightness is maintained by not the adhesion between packing 125 and rod 112 but by the adhesion between packing 125 adhering to the inner wall of decompression chamber 150 and packing 113. Adhesion between packing materials (here packing 125 and packing 113) provides strong airtightness. When pressure reduces, airtightness increases.

Figure 9D:
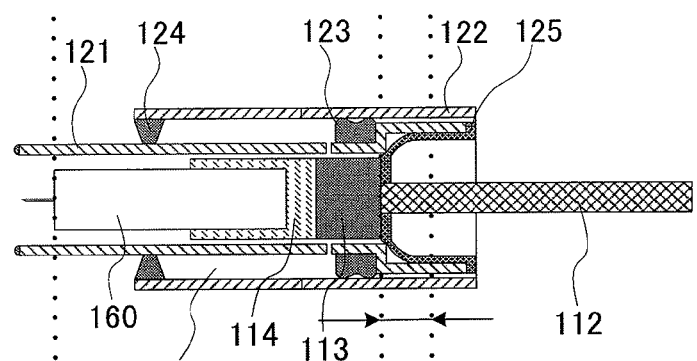

FIG. 9D shows a state in which puncturing is being performed. As shown by the arrows in FIG. 9D, two kinds of force, force to push packing 125 into decompression chamber 150 and the force of a spring (not shown) in needle puncturing device 100, are applied to puncturing needle 160 to be moved.

Figure 9E:
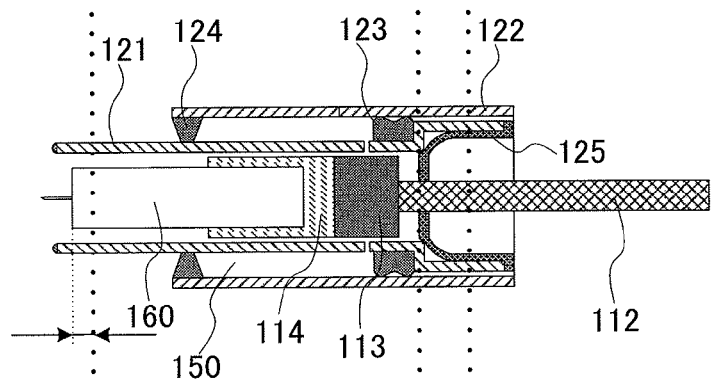

FIG. 9E shows a state in which puncturing needle 160 maximally extends. As shown in FIG. 9E, puncturing needle holder 114 slides in only the distance to which puncturing needle 160 extends. This uses the inertia force produced by moving puncturing needle 160 and puncturing needle holder.

Figure 9F:
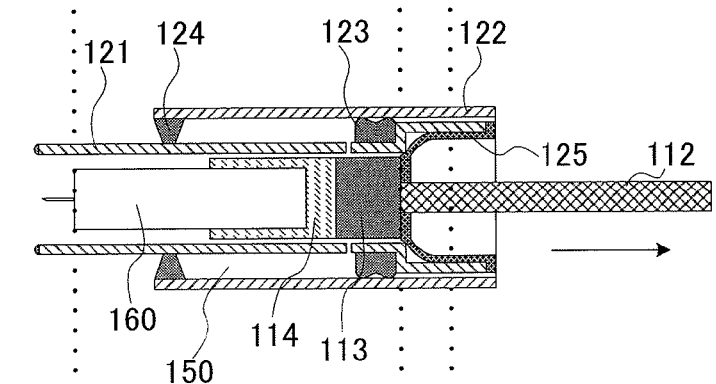

FIG. 9F shows a state in which puncturing needle returns to a predetermined position. As shown by the arrows in FIG. 9F, puncturing needle 160 returns to the initial position by means of a needle return mechanism in needle puncturing device 100 (cam mechanism using pull spring 111d: see FIG. 7).

Puncturing operation of needle puncturing device 100 and decompression operation of decompression and blood sampling mechanism 120 have been explained.

Now, variations of components in decompression and blood sampling mechanism 120 will be explained.

FIG. 10A, FIG. 10B and FIG. 10C (hereinafter collectively referred to as FIG. 10) each show another configuration example of the packing configuration of piston 121.

FIG. 10A shows the same packing configuration as in piston 121 shown in FIG. 7. Piston 121 has packing 123 on the outer surface and packing 125 on the inner surface.

In addition, as shown in FIG. 10B, a configuration is possible where packing 123 and packing 125 are combined and made of the same member to make packing 125A.

Moreover, as shown in FIG. 10C, another configuration is possible where packing 123 and packing 125 are combined and made of the same member to make packing 125B. Packing 125B is attached to the end part of piston 121B. As compared to piston 121, piston 121B does not have a step part projecting outward, and therefore has an advantage that it is easily introduced. Here, packing 125B needs to have a sufficient area to adhere to the outer surface of piston 121B in order not to drop due to force applied in the sliding direction.

FIG. 11A and FIG. 11B (hereinafter collectively referred to as FIG. 11) and FIG. 12A and FIG. 12B (hereinafter collectively referred to as FIG. 12) are cross sectional views each showing an anti-shake puncturing needle guide attached to piston 121.

FIG. 11A is a cross sectional view parallel to the axial direction of rod 112, and FIG. 11B is a cross sectional view vertical to the axial direction of rod 112, in anti-shake puncturing needle guide 127 and its nearby parts.

As shown in FIG. 11B, piston 121 has grooves 121e along the sliding direction of puncturing needle 160. Grooves 121e are provided evenly on the left, right, top and bottom of the inner surface of piston 121. Convex parts 114a are provided on the left, right, top and bottom of puncturing needle holder 114, which are slidably fitted into those grooves 121e. Grooves 121e in piston 121 and convex parts 114a on puncturing needle holder 114 constitute anti-shake puncturing needle guides 127, respectively. By providing anti-shake puncturing needle guides 127, it is possible to prevent puncturing needle 160 from shaking at the time of puncturing.

In addition, as shown in FIG. 12, piston 121C has upper groove 121e and lower grooves 121f along the sliding direction of puncturing needle 160. Upper groove 121e is provided in a predetermined position (referred to as "top" for ease of explanation) in the inner surface of piston 121C. Lower grooves 121f are notch parts and provided in two predetermined positions (referred to as "bottoms" for ease of explanation) in the inner surface of piston 121C. Upper groove 121e and lower grooves 121f are provided in the positions in the inner surface of piston 121C at even intervals resulting from dividing the inner surface by 3.

Puncturing needle holder 114 has spring-like convex part 114 slidably fitted into upper groove 121e and protrusions 114c slidably fitted into lower grooves 121f.

Upper groove 121e in piston 121C and spring-like convex parts 114b in puncturing needle holder 114 constitute upper anti-shake puncturing needle guide 127a, and lower grooves 121f in piston 121C and protrusions 114c on puncturing needle holder 114 constitute lower anti-shake puncturing needle guide 127b.

Upper anti-shake puncturing needle guide 127a prevents puncturing needle 160 from shaking at the time of puncturing, and, as shown by the arrows in FIG. 12B, allows spring-like convex part 114b to always generate downward force. This downward force is uniformly applied to a plurality of lower anti-shake puncturing needle guides 127b arranged evenly.

By providing upper anti-shake puncturing needle guide 127a and lower anti-shake puncturing needle guides 127b, it is possible to prevent puncturing needle 160 from shaking at the time of puncturing.

Here, although a case is shown in FIG. 12B where grooves are provided in three positions, the present invention is not limited to this naturally. If the number of positions is more than 4, it is possible to prevent shaking.

Figure 13:
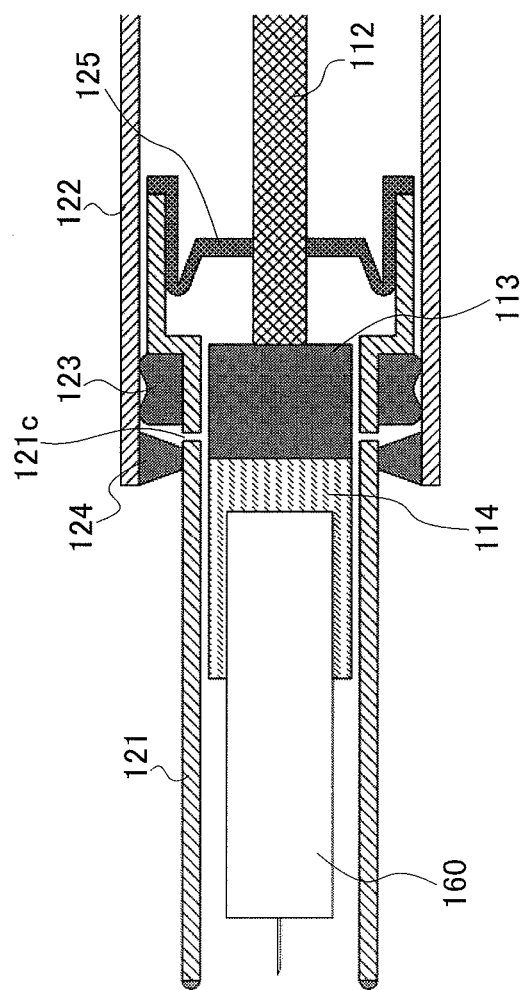
FIG. 13 shows the shape of a packing fixed to a puncturing needle holder in the puncturing device according to Embodiment 1.

FIG. 13 and FIG. 14 (collective name of FIG. 14A, FIG. 14B, FIG. 14C and FIG. 14D) each explain the shape of packing 113 fixed to puncturing needle holder 114.

FIG. 13 shows a comparative example to explain a variation of the shape of packing 113 shown in FIG. 14, and shows the same components as in the above-described FIG. 7.

As shown in FIG. 13, basically, the side surface of packing 113 adheres to the side surface of packing 125 to maintain the airtightness at the time of pressure reduction. The side surface of packing 113 or the side surface of packing 125 has an innovative shape, so that it is possible to effectively improve adhesion (airtightness) at the time of pressure reduction.

Figure 14A:
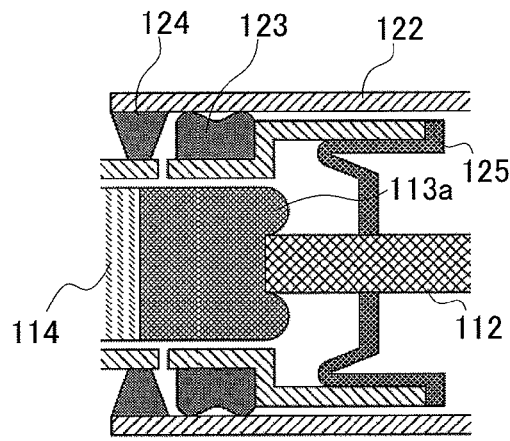
FIGS. 14A, B, C and D each show the shape of a packing fixed to a puncturing needle holder in the puncturing device according to Embodiment 1.

As shown in FIG. 14A, packing 113a fixed to puncturing needle holder 114 has ring-like semicircular protrusions around rod 112. Likewise, although illustration is omitted, ring-like semicircular protrusions may be provided on the side surface of packing 125. With this configuration, it is possible to further improve the adhesion between packing 113a and packing 125.

Figure 14B:
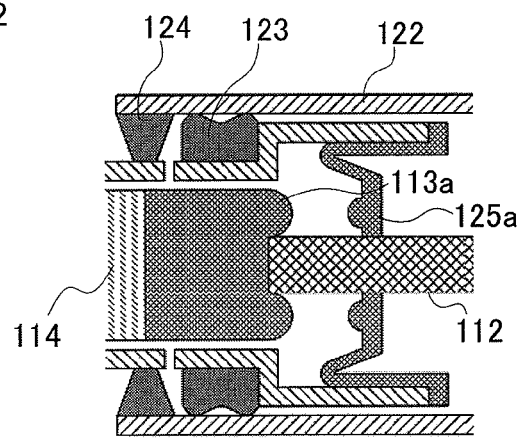

Next, as shown in FIG. 14B, packing 125a has ring-like semicircular protrusions around rod 112, on the side surface facing packing 113a. With this configuration, it is possible to further improve the adhesion between packing 113a and packing 125.

Here, packing 113a may not be made of an elastic material, but may be made of the same material as puncturing needle holder 114.

Figure 14C:
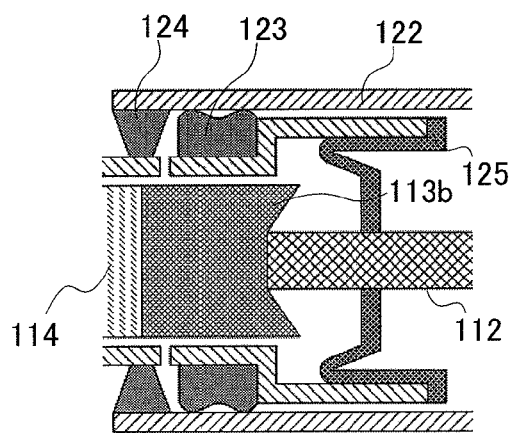

As shown in FIG. 14C, packing 113b fixed to puncturing needle holder 114 has sucker-like protrusions on the outer surface, which adsorb to the side surface of packing 125. Packing 113b has a sucker-like structure and packing 125 has a planar side surface, and therefore, when packing 113b adheres to packing 125, it is possible to improve adhesion even if pressure cannot be satisfactorily reduced.

Here, the surface of packing 125 attaching to packing 113b may not necessarily be made of an elastic material.

Figure 14D:
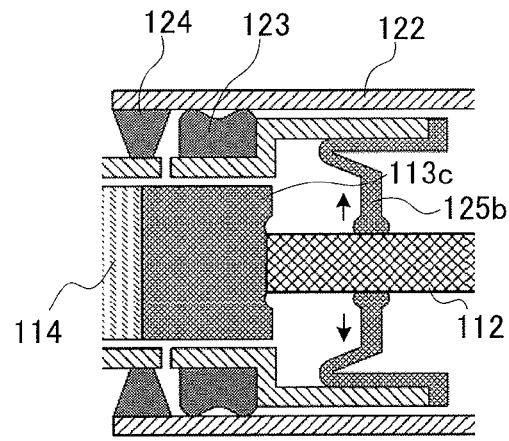

As shown in FIG. 14D, packing 113c fixed to puncturing needle holder 114 has ring-like concave parts around rod 112. Meanwhile, packing 125b has ring-like convex parts to fit into the concave parts in packing 113c. Each convex part on packing 125b has an end surface that slides on rod 112 and is thicker than other parts. In the present example, packing 125b is also provided with the same convex parts in the back side as the ring-like convex parts fitting into the concave parts in packing 113c. The part contacting between packing 113c and rod 112 is slightly thicker than other parts for the purpose of sliding.

By the way, in a state in which pressure is reduced, force of air to flow in is applied to generate force to raise the decompression chamber side 150. As shown in FIG. 14D, the side surface of packing 125b and the side surface of packing 113c hold the relationship of convex and concave in shape, so that it is possible to prevent the above-described rising. In addition, when puncturing needle 160 returns to the original position by a needle return mechanism (cam mechanism using pull spring 111d shown in FIG. 7) in needle puncturing device 100, an advantage of minimizing air inflow is provided.

As described above in detail, according to the present embodiment, needle puncturing device 100 has piston 121 having one end part 121a forming part of sensor mounting mechanism 130 and the other end part 121b that slidably supports rod 112 in lancet section 111; cylinder 122 that slidably accommodates end part 121b in piston 121 inside; and packing 125 that is attached to the inner surface of end part 121b in piston 121 and maintains the airtightness around rod 112. When piston 121 moves toward cylinder 122 while skin contacting part 131 contacts skin, the volume of internal space 140 and decompression chamber 150 sealed with packing 123 and packing 124 increases to reduce pressure, and at this time, packing 125 uses force applied to the inside of decompression chamber 150 to operate rod 112. By this means, it is possible to desirably reduce pressure with simple operation, and consequently improve operability. Now, advantages will be described in detail.

Conventionally, in a decompression and blood sampling method used in needle puncturing, a lancet system is generally provided in a decompression chamber. That is, in a system in which a puncturing needle is operated to perform puncturing, it is necessary to smoothly move a puncturing needle, and, when a puncturing mechanism is provided out of a decompression chamber, it is necessary to move a needle while a constant sealed state is made between the decompression chamber and a moving section. The relationship between sealing force and the resistance of a moving section is that, when sealing force is greater, the resistance of a moving section increases. A lancet system requires a considerably large power to move a puncturing needle to the position in which puncturing can be performed.

With the present embodiment, needle puncturing device 100 (see FIG. 7) has decompression and blood sampling mechanism 120 (see FIG. 7), and packing 125 maintains the airtightness between decompression mechanism 120 and puncturing operation activating mechanism 110 (see FIG. 7 and FIG. 8). That is, even if decompression and blood sampling mechanism 120 reduces the pressure inside, the pressure in puncturing operation activating mechanism 110 does not reduce, so that the parts in which pressure is reduced are only internal space 140 in decompression and blood sampling mechanism 120 and decompression chamber 150, and therefore the volume in which pressure is reduced is small. This provides a specific effect that it is possible to reduce pressure only by pushing skin contacting part 131 to the apparatus body side.

In addition, packing designed to apply force to the inside of decompression chamber 150 at the time of pressure reduction, is provided on a part connecting decompression chamber 150 with an external part (lancet section 111), and the force of packing 125 trying to sink into decompression chamber 150 is used to move lancet section 111 (see FIG. 7) and to maintain airtightness. By using this method, it is possible to perform puncturing without strengthening puncturing spring 111d (see FIG. 7) provided in lancet section 111.

Moreover, with the present embodiment, it is possible to reduce pressure and sample blood only by pushing the part having been punctured to skin puncturing part 131 in piston 121 and pushing piston 121 into the apparatus body side, and, when the required amount of blood is obtained, air pressure adjustment to make the pressure similar to the atmosphere pressure is performed by weakening the pushing force to separate skin 18 from the apparatus in a series of operation, and therefore blood does not scatter due to rapid air inflow.

(Embodiment 2)

Figure 15A:
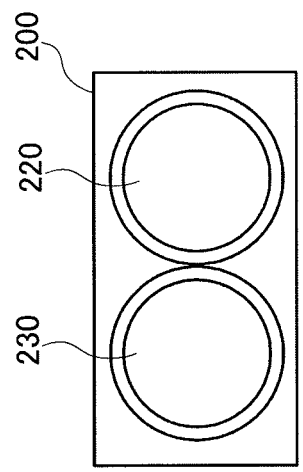
FIG. 15 shows a conceptual diagram explaining the difference in the configuration between Embodiment 1 and Embodiment 2 according to the present invention.
Figure 15B:
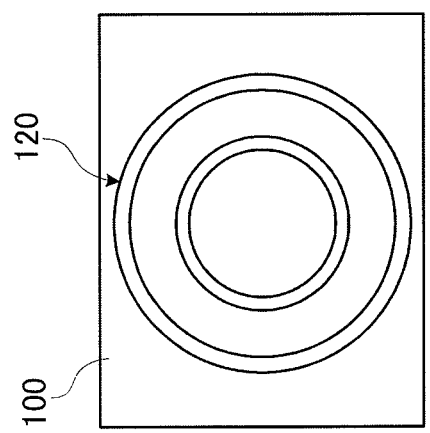

FIG. 15 is a conceptual diagram explaining the difference in the configuration between Embodiment 1 and Embodiment 2. FIG. 15A is a cross sectional view schematically showing needle puncturing device 100 according to Embodiment 1, and FIG. 15B is a cross sectional view schematically showing needle puncturing device 200 according to Embodiment 2.

As shown in FIG. 15A, decompression and blood sampling mechanism 120 according to Embodiment 1 is direct acting type in which "puncturing mechanism" and "decompression mechanism" are provided concentrically. Meanwhile, with Embodiment 2, puncturing mechanism 220 and decompression mechanism 230 are provided in parallel. The dimension (especially, thickness) of needle puncturing device 200 according to Embodiment 2 can be smaller than that of needle puncturing device 100 according to Embodiment 1.

Figure 16:
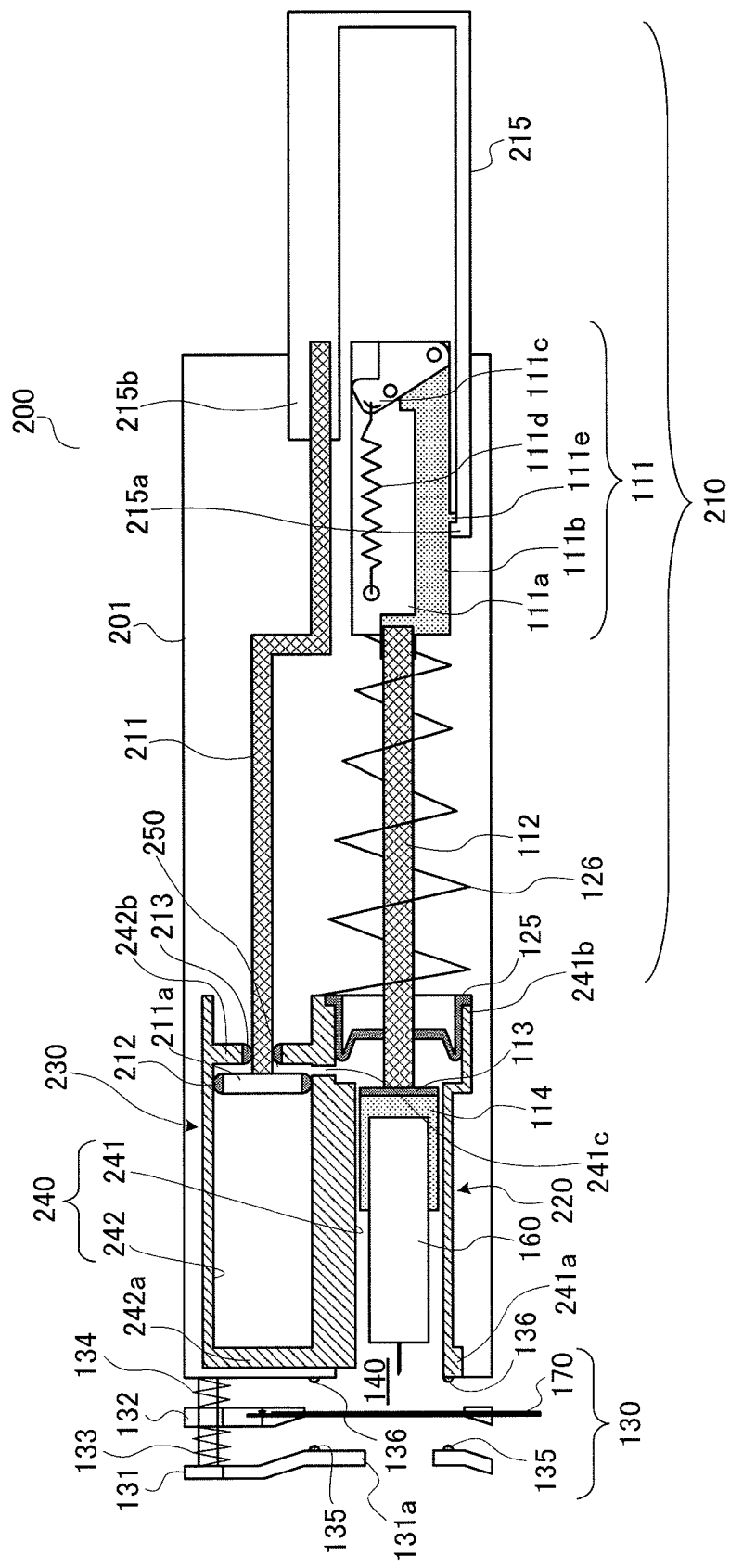
FIG. 16 is a cross sectional view showing a puncturing device according to Embodiment 2 of the present invention.

FIG. 16 is a cross sectional view showing a puncturing device according to Embodiment 2 of the present invention. The same components as in FIG. 7 are assigned the same reference numerals, and overlapping descriptions will be omitted.

As shown in FIG. 16, needle puncturing device 200 has a configuration to mainly include: housing 201; puncturing operation activating mechanism 210 that is provided in housing 201 and outside a decompression and blood sampling mechanism and allows puncturing needle 160 to perform puncturing; puncturing mechanism 220 that punctures skin through held sensor 170; decompression mechanism 230 that is provided in parallel with puncturing mechanism 220 and reduces the pressure in space formed by contacting skin; and sensor mounting mechanism 130.

First, puncturing operation activating mechanism 210 will be explained.

Puncturing operation activating mechanism 210 is provided out of puncturing mechanism 220 and decompression mechanism 230, and has lancet section 111 that allows puncturing needle 160 to perform puncturing; rod 112 that transfers puncturing operation of lancet section 111 to puncturing needle 160; and knob 215 that transfers charging operation of lancet section 111 to rod 112 and transfers decompression operation of decompression mechanism 230 to rod 211.

Lancet section 111 has base plate 111a to which plunger 111b, lever 111c and pull spring 111d are attached. Rod 112 is connected to plunger 111b and can slide in a predetermined range of puncturing mechanism cylinder 241 (described later) in puncturing mechanism 220 in conjunction with movement of plunger 111b. Plunger 111b returns to the natural state by rotating lever 111c biased by pull spring 111d.

Knob 215 is formed in hollow to cover the entire lancet section 111. When pull spring 111d is charged, one end part 215a of knob 215 engages with protrusion 111e on plunger 111b and pulls lancet section 111 outside housing 201 (puncturing needle 160 is moved to the right in FIG. 16) to charge lancet section 111 to be able to perform puncturing. In addition, the other end part 215b of knob 215 is connected to rod 211 and pushes rod 211 into housing 201 (moves rod 211 to the left hand in FIG. 16) to allow decompression mechanism 230 to reduce pressure at the time of pressure reduction. In operation at the time of pressure reduction, end part 215b in knob 215 moves to the direction in which end part 215a separates from protrusion 111e on plunger 111b. In addition, lancet section 111 does not contact the inner surface of knob 215 in end part 215b. Therefore, knob 215 does not influence charging operation.

Moreover, puncturing operation activating mechanism 210 is provided in puncturing mechanism 220, and has packing 113 provided on end part 112a of rod 112 and puncturing needle holder 114 attached to packing 113 to mount puncturing needle 160.

Next, puncturing mechanism 220 and decompression mechanism 230 will be explained.

Each of puncturing mechanism 220 and decompression mechanism 230 is a decompression mechanism based on basically the same principle as of decompression and blood sampling mechanism 120 described with reference to FIG. 7. With Embodiment 2, decompression and blood sampling mechanism 120 (FIG. 7) is divided into "puncturing mechanism" and "decompression mechanism", and these are provided in parallel.

Puncturing mechanism 220 has puncturing mechanism cylinder 241 in the sensor mounting mechanism 130 side in housing 201. Meanwhile, decompression mechanism 230 has decompression mechanism cylinder 242 provided parallel to puncturing mechanism cylinder 241. With the present embodiment, puncturing mechanism cylinder 241 and decompression mechanism cylinder 242 are integrally formed as cylinder block 240. Here, puncturing mechanism cylinder 241 and decompression mechanism cylinder 242 may be separately formed as long as these are provided in parallel in housing 201.

[Puncturing Mechanism 220]

In puncturing mechanism 220, puncturing operation activating mechanism 210 operates a puncturing needle in puncturing mechanism cylinder 241.

Puncturing mechanism cylinder 241 has one end part 241a forming part of sensor mounting mechanism 130, the other end part 241b slidably supporting rod 112 in lancet section 111 and connection hole 241c that supplies the pressure reduced by decompression mechanism 230 into puncturing mechanism cylinder 241.

Second packing 136 is attached to end part 241a to seal between sensor 170 and puncturing mechanism 220. When skin contacts skin contacting part 131 in sensor mounting mechanism 130, second packing 136 maintains the airtightness of cylindrical internal space 140 closed by contacting skin.

Packing 125 to maintain the airtightness around rod 112 is attached to the inner surface and opening in end part 241b.

Connection hole 241c connects the sealed space formed by packing 125 that maintains the airtightness between the inner surface of tubular end part 241b and the outer surface of rod 112 and packing 113 provided in end part 112a in rod 112 with decompression chamber 250 (see FIG. 17C and FIG. 17D) in decompression mechanism 230. As seen from the puncturing mechanism 220 side, connection hole 241c is always sealed with packing 125 and packing 113 and is open in the position to connect to decompression chamber 250, regardless of the sliding state of rod 112. Therefore, connection hole 241c is open between packing 125 and packing 113 in the natural state. Here, packing 125 more securely maintains the reduced pressure state by adhering to packing 113 at the time of pressure reduction.

Puncturing mechanism 220 has spring 126 that biases cylinder block 240 to return to the original state at all times.

[Decompression Mechanism 230]

Decompression mechanism 230 reduces the pressure in decompression mechanism cylinder 242 by movement of rod 211 in conjunction with decompression operation by pushing knob 215.

Decompression mechanism cylinder 242 has one end part 242a that forms part of sensor mounting mechanism 130 and the other end part 242b that slidably supports rod 211 moving at the same time as knob 215 is pushed. In addition, a vent (not shown) is open in end part 242a to remove air in decompression mechanism cylinder 242 at the time of pressure reduction.

End part 211a of rod 211 has a circular disk shape and slides following movement of rod 211 in decompression mechanism cylinder 242. Packing 212 is attached to the outer surface of end part 211a.

Packing 213 to maintain the airtightness between decompression chamber 250 and the outer surface of rod 211 is attached to the opening and inner surface of end part 242b.

Sealed space formed by packing 213 attached to the inner surface of tubular decompression mechanism cylinder 242 and the inner surface of end part 242b and packing 212 attached to the outer surface of end part 211a in rod 211 forms decompression chamber 250 that reduces pressure.

As seen from the decompression mechanism 230 side, connection hole 241c is open in a position to connect decompression camber 250 always sealed with packing 212 and packing 213 regardless of the sliding state of end part 211a in rod 211. Therefore, connection hole 241c is open between packing 212 and packing 213 in the natural state.

Now, puncturing operation of needle puncturing device 200 configured as described above, will be explained.

First, basic puncturing operation will be explained.

FIG. 17A, FIG. 17B, FIG. 17C, FIG. 17D and FIG. 17E (hereinafter collectively referred to as FIG. 17) each explain puncturing operation of needle puncturing device 200.

Figure 17A:
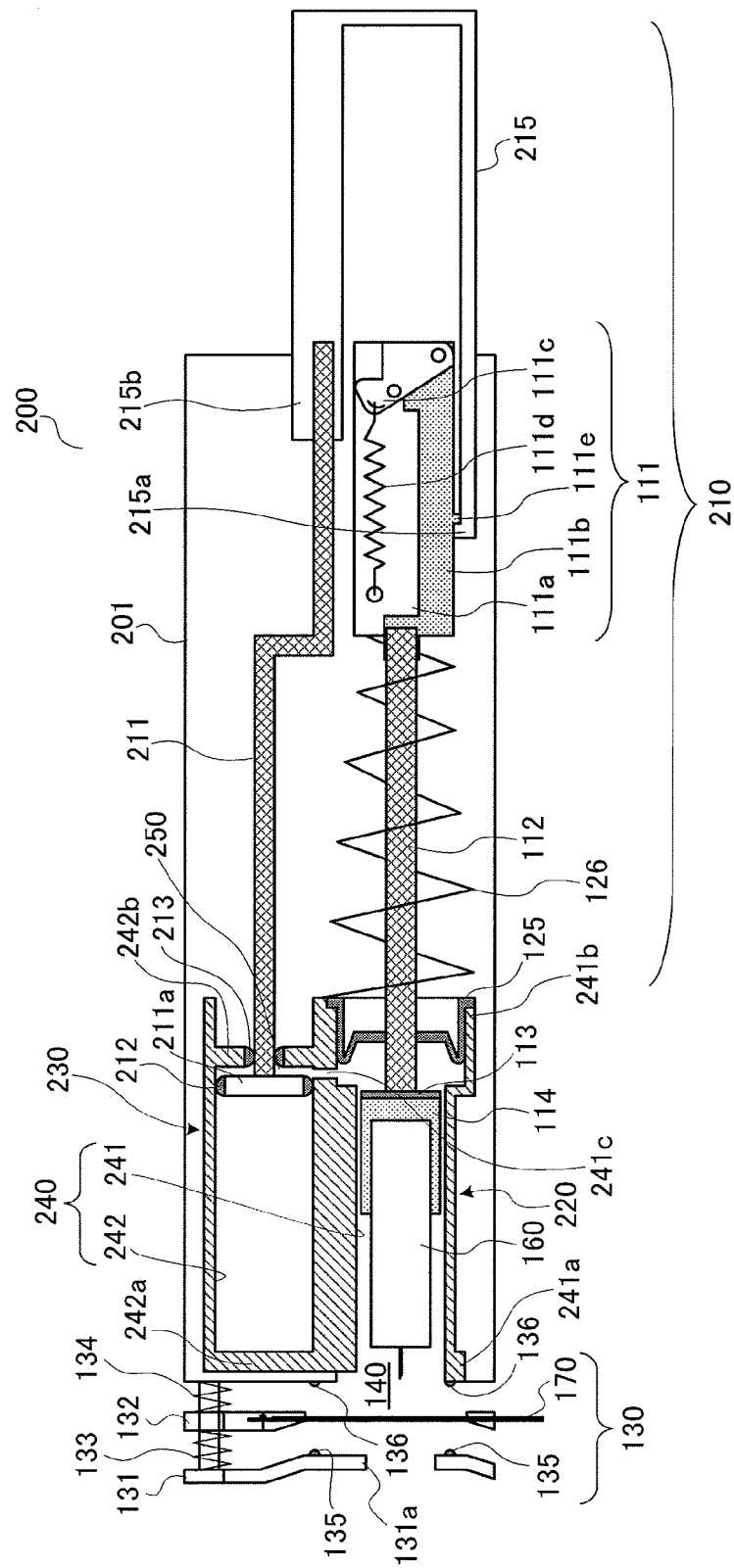
FIG. 17A explains puncturing operation of the puncturing device according to Embodiment 2.

As shown in FIG. 17A, sensor 170 is mounted in sensor mounting mechanism 130.

Figure 17B:
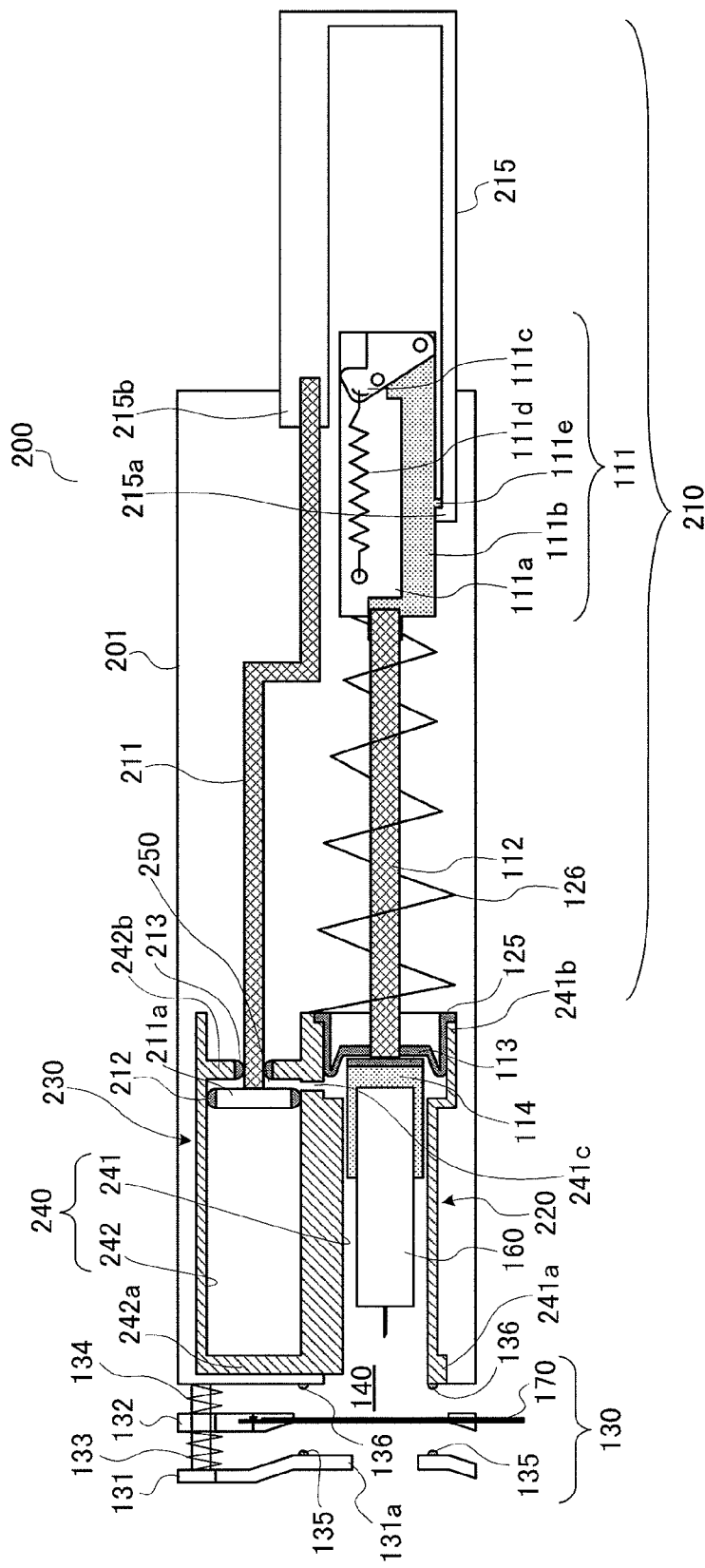
FIG. 17B explains puncturing operation of the puncturing device according to Embodiment 2.

Next, as shown in FIG. 17B, lancet section 111 in puncturing operation activating mechanism 210 is pulled out of housing 201 (puncturing needle 160 is moved to the right in FIG. 17B) to be charged to be able to perform puncturing. To be more specific, end part 215a in knob 215 engages with protrusion 111e on plunger 111b and lancet section 111 is pulled out of housing 201 to charge pull spring 111d in lancet section 111. Packing 113 adheres to packing 125.

Figure 17C:
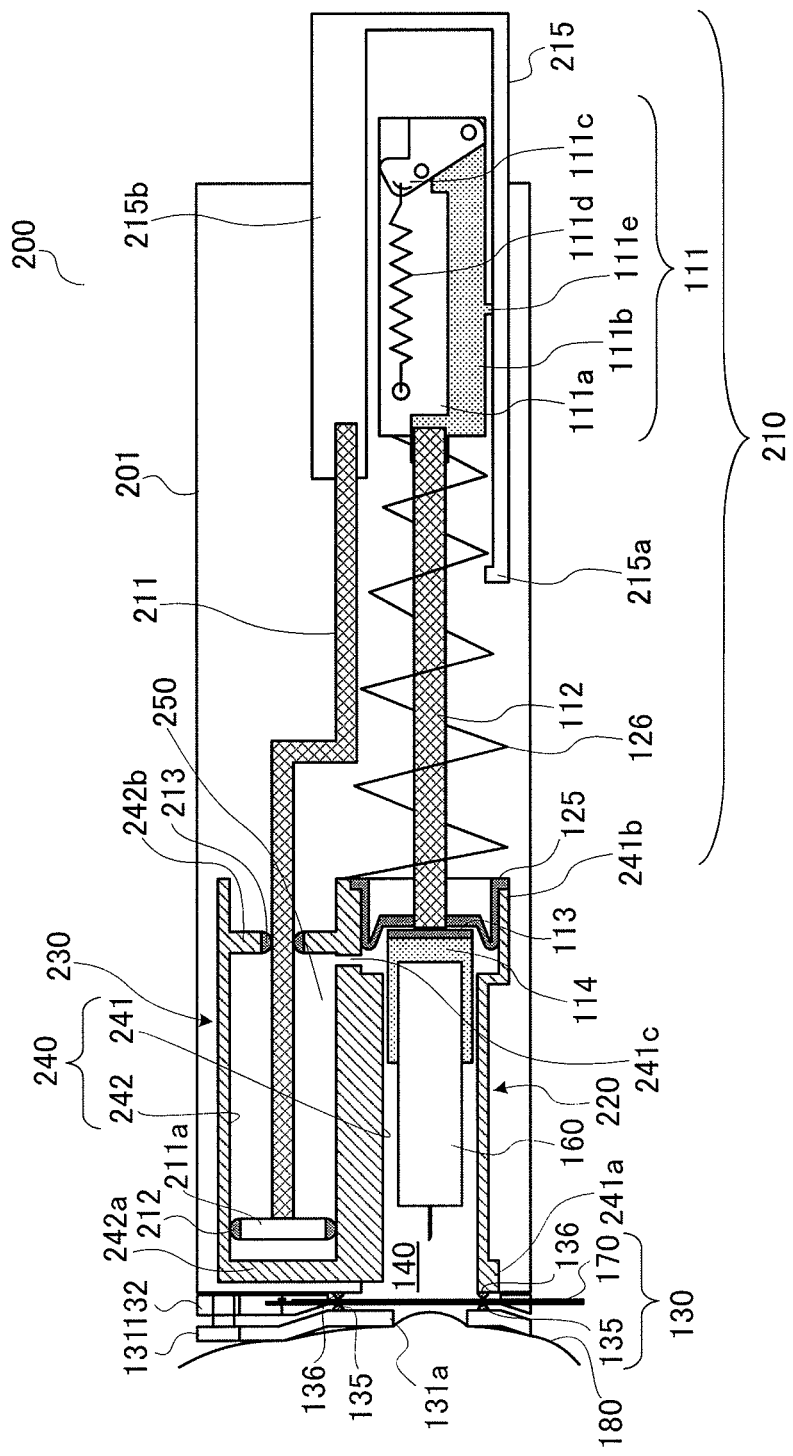
FIG. 17C explains puncturing operation of the puncturing device according to Embodiment 2.

As shown in FIG. 17C, skin 180 of a finger (or palm, upper arm) is pushed against skin contacting part 131 in sensor mounting mechanism 130 to secure the airtightness in cylindrical internal space 140 in puncturing mechanism cylinder 241. By this means, it is possible to secure also the airtightness in the sealed space formed by packing 125 to maintain the airtightness between the inner surface of tubular end part 241b and the outer surface of rod 112 and packing 113 attached to end part 112a in rod 112.

In this state, the user pushes knob 215 into housing 201 by, for example, pressing operation with the thumb (rod 211 is moved to the left in FIG. 17C). End part 211a in rod 211 slides in decompression mechanism cylinder 242 to reduce the pressure in decompression chamber 250 in decompression mechanism cylinder 242. Decompression chamber 250 is connected to puncturing mechanism cylinder 241 through connection hole 241c. Therefore, the pressure in the sealed space formed by the inner surface of tubular end part 241b in puncturing mechanism cylinder 241, packing 125 and packing 113, is also reduced. This pressure reduction allows packing 125 and packing 113 to more tightly adhere to one another. The pressure in the above-described sealed space in puncturing mechanism cylinder 241 is reduced, and therefore the pressure in cylindrical internal space 140 is reduced.

The above-described sealed space formed by the inner surface of tubular end part 241b in puncturing mechanism cylinder 241, packing 125 and packing 113, and cylindrical internal space 140 connecting to the sealed space constitute space targeted for pressure reduction in puncturing mechanism 220. That is, decompression mechanism 230 reduces the pressure in the above-described sealed space through connection hole 241c in decompression chamber 250, and reduces the pressure in cylindrical internal space 140 at the same time. The above-described sealed space may be referred to as narrowly defined space targeted for pressure reduction.

Figure 17D:
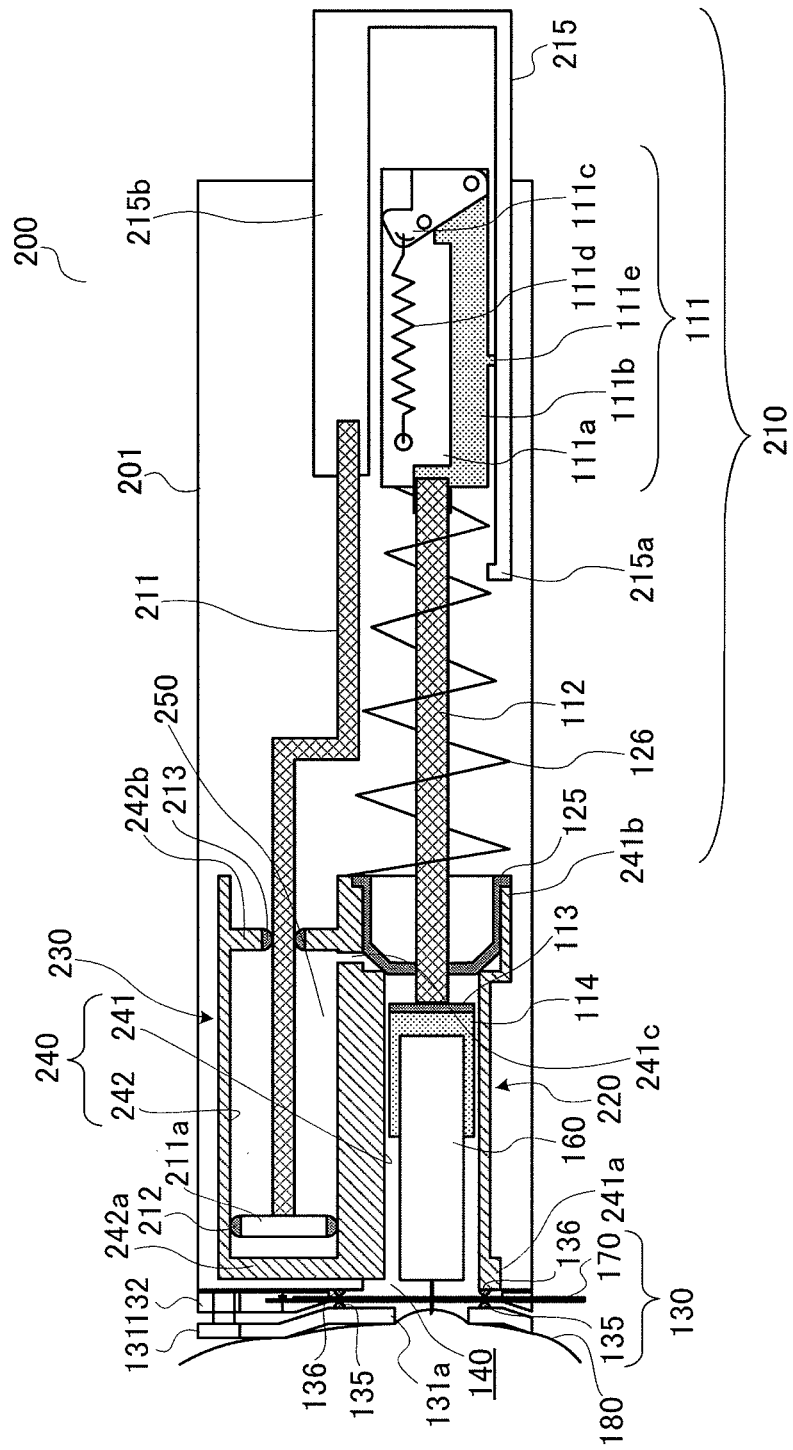
FIG. 17D explains puncturing operation of the puncturing device according to Embodiment 2.

FIG. 17D shows puncturing operation. At the time of puncturing, packing 125 sinks into the above-described sealed space in puncturing mechanism cylinder 241 and moves puncturing needle 160 by this sinking force. In addition, puncturing needle 160 further projects by inertia.

Figure 17E:
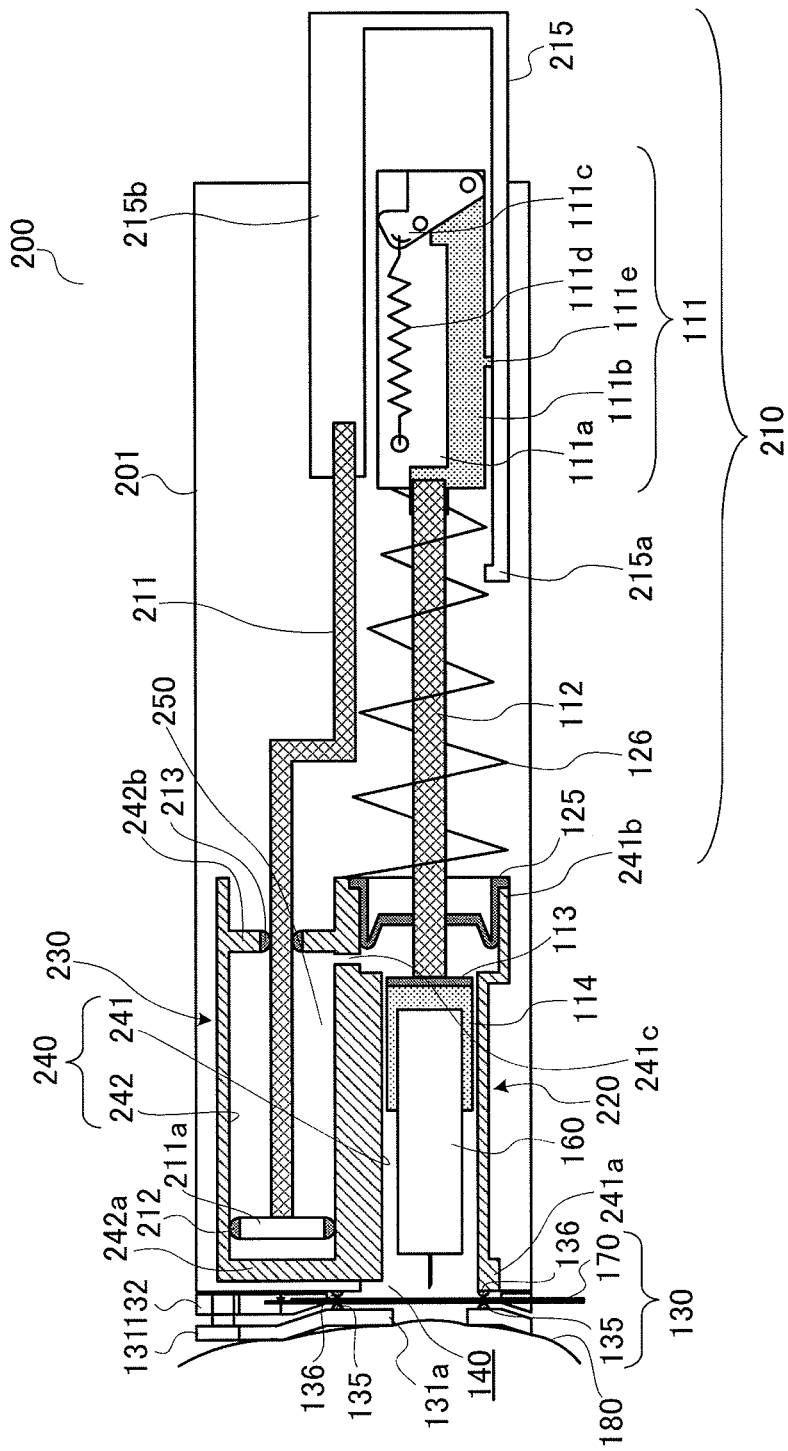
FIG. 17E explains puncturing operation of the puncturing device according to Embodiment 2.

After puncturing needle 160 punctures skin 180, blood exuding from the surface of skin 180 is introduced into sensor 170 as shown in FIG. 17E, and then measurement starts. In addition, a cam mechanism (not shown) in lancet section 111 returns puncturing needle 160 to the position before charging.

Needle puncturing device 200 according to the present embodiment is compact and light, and has a shape to help the user's grasp. When the user holds needle puncturing device 200 according to the present embodiment by hand, it is possible to reduce pressure by moving the thumb up and down. This decompression operation by moving the thumb up and down provides an advantage that the user can intuitively and easily operate the device.

In addition, needle puncturing device 200 has puncturing mechanism 220 and decompression mechanism 230 provided in parallel, and therefore can reduce its size (especially, thickness).

(Embodiment 3)

Embodiment 3 is an example of a puncturing device having a puncturing needle removing mechanism.

FIG. 18A is a cross sectional view showing a puncturing device according to Embodiment 3 of the present invention, and FIG. 18B is a side view of FIG. 18A from the direction of the arrow. FIG. 19A is a cross sectional view showing the puncturing device at the time of removing operation, and FIG. 19B is a side view of FIG. 19A from the direction of the arrow. The same components as in FIG. 16 are assigned the same reference numerals, and overlapping descriptions will be omitted.

As shown in FIG. 18A and FIG. 18B, needle puncturing device 300 is provided in housing 201, and has puncturing operation activating mechanism 210 that is provided out of a decompression and blood sampling mechanism and allows puncturing needle 160 to perform puncturing, and puncturing needle removing mechanism 350 that removes puncturing needle 160.

Puncturing operation activating mechanism 210 has knob 315 that transfers charging operation of lancet section 111 to rod 112 and transfers decompression operation of decompression mechanism 230 to rod 211. Knob 315 is formed in hollow to cover the entire lancet section 111 and accommodates lancet section 111 in the space.

Puncturing needle removing mechanism 350 is realized by the following components provided in knob 315.

As shown in FIG. 18B and FIG. 19B, knob 315 has a cylindrical shape with a bottom and can rotate around the central axis of the cylindrical body. Knob 315 has semicircular opening 315b and arc opening 315c in bottom 315a of the cylindrical body. End part 316a in rod 316 is fixedly provided toward the central axis from any position in opening 315b in bottom 315a. As shown in FIG. 18A and FIG. 19A, one end part 316a in rod 316 is fixed to bottom 315a and the other end 316b contacts the bottom of lancet section 111 at the time a puncturing needle is removed. That is, knob 315 has rod 316 that is apart from the central axis by a predetermined distance in parallel with the central axis. End part 316b in rod 316 rotates to be apart from the bottom of lancet section 111 when a puncturing needle is mounted as shown in FIG. 18B, and, on the other hand, rotates to contact the bottom of lancet section 111 when a puncturing needle is removed as shown in FIG. 19B.

In addition, as shown in FIG. 18B and FIG. 19B, rod 211 is accommodated in arc opening 315c such that bottom surface 211a of rod 211 is exposed. Rod 211 is accommodated in arc opening 315b, so that the rotating range of knob 315 is limited. In addition, it is possible to check if a puncturing needle is removed or mounted, based on the position of bottom surface 211a of rod 211 exposed to opening 315c.

Here, although illustration is omitted, it is preferable to show, for example, carve a message indicating whether a puncturing needle is mounted or removed, on bottom 315a. Moreover, bottom surface 211a of rod 211 may be colored with a distinct color.

As shown in FIG. 18A and FIG. 18B, when a puncturing needle does not need to be removed, the user does not rotate knob 315. Bottom surface 211a of rod 211 is apart from the bottom of lancet section 111, and therefore, lancet section 111 is not influenced by rod 211, like puncturing operation of needle puncturing device 200 according to Embodiment 2 (see FIG. 17).

As shown in FIG. 19A and FIG. 19B, when a puncturing needle is removed, the user rotates knob 315. To be more specific, the user rotates knob 315 until bottom surface 211a of rod 211 moves from one end of arc opening 315c to the other end. As shown in FIG. 19B, end part 316b in rod 316 contacts the bottom of lancet section 111.

In this state, the user pushes knob 315 deeply into housing 201 as shown in FIG. 19A. Lancet section 111 contacting rod 316 moves puncturing needle 160 widely to the left, and therefore puncturing needle 160 is pushed out of housing 201. By this means, it is possible to remove puncturing needle 160.

As described above, according to the present embodiment, needle puncturing device 300 has puncturing needle removing mechanism 350 formed by components of knob 315 and components of rod 316, and therefore provides an advantage that it is possible to easily and quickly remove puncturing needle 160. The user can easily set mount or removal of a puncturing needle in puncturing needle removing mechanism 350 only by rotating knob 315.

Here, although with the present embodiment, a configuration has been explained where end part 316b in rod 316 contacts the bottom of lancet section 111 by rotating knob 315, another configuration is possible where rod 316 slides to the bottom of lancet section 111.

(Embodiment 4)

Embodiment 4 is a configuration example in which a sensor holding part can be removed from the apparatus body.

Figure 20A:
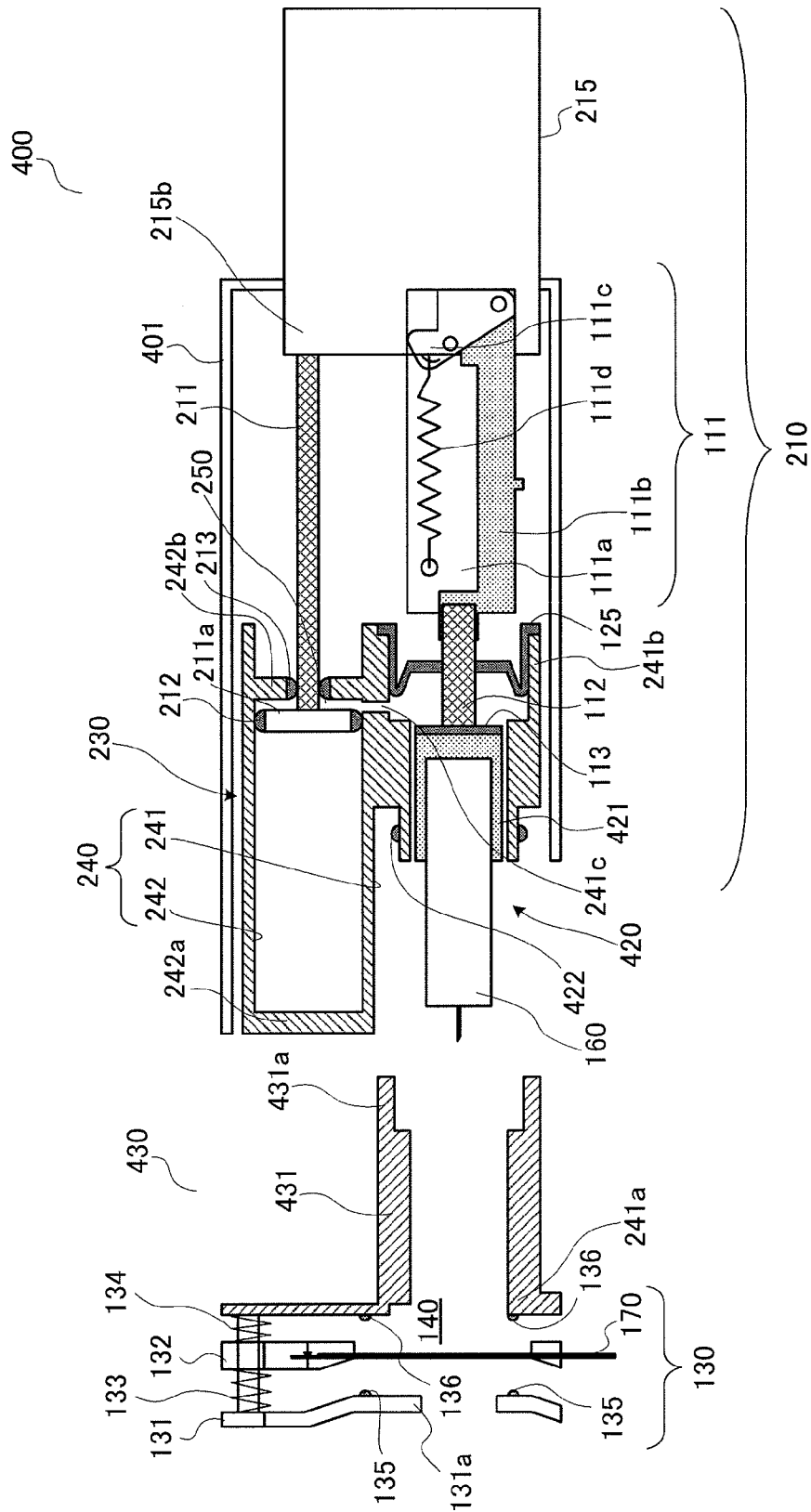
FIG. 20A shows a puncturing device according to Embodiment 4 of the present invention.
Figure 20B:
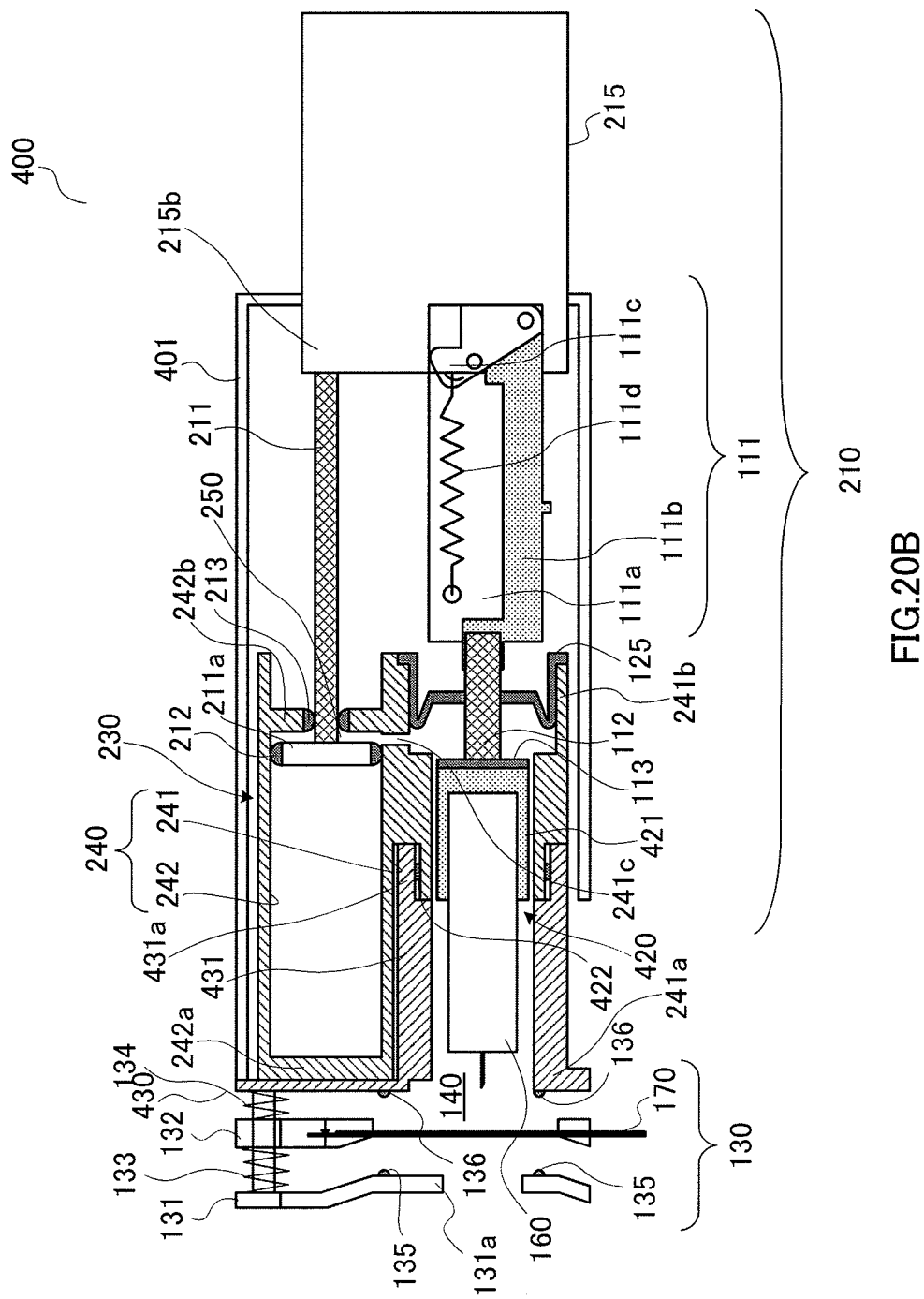
FIG. 20B shows the puncturing device according to Embodiment 4.

FIG. 20A is a cross sectional view showing a puncturing device according to Embodiment 4 of the present invention, and FIG. 20B is a cross sectional view showing the puncturing device at the time of removing operation. The same components as in FIG. 16 are assigned the same reference numerals, and overlapping descriptions will be omitted.

As shown in FIG. 20A and FIG. 20B, needle puncturing device 400 has a configuration to mainly include: housing 401; puncturing operation activating mechanism 210 that is provided in housing 401 and outside a decompression and blood sampling mechanism, and allows puncturing needle 160 to perform puncturing; puncturing mechanism 420 that punctures skin through held sensor 170; decompression mechanism 230 that is provided parallel to puncturing mechanism 220 and reduces the pressure in the space formed by contacting skin; and sensor mounting mechanism 430 that can be removed from housing 401.

Here, in order to make the size of needle puncturing device 400 smaller than needle puncturing device 200 shown in FIG. 16, the entire length of housing 401, the length of rod 112 and the length of rod 211 are shorter than in needle puncturing device 200 (FIG. 16). The same reference numerals as in FIG. 16 are assigned for ease of explanation.

In addition to the components of sensor mounting mechanism 130 shown in FIG. 16, sensor mounting mechanism 430 further includes mounting part 431 that removably mounts a puncturing needle in puncturing mechanism 420. Mounting part 431 constitutes a cylindrical half part (the left half in FIG. 20A and FIG. 20B) of puncturing mechanism cylinder 241 in puncturing mechanism 220 shown in FIG. 16. Mounting part 431 has a step formed by reducing the thickness of opening 431a in the cylindrical body.

Puncturing mechanism 420 has mounting part 421 that engages with mounting part 431 in sensor mounting mechanism 430. Packing 422 is attached to the outer surface of the cylindrical body of mounting part 421 facing opening 431a in mounting part 431 in sensor mounting mechanism 430. Packing 422 maintains the airtightness between sensor mounting mechanism 430 and puncturing mechanism 420.

As shown in FIG. 20A, sensor mounting mechanism 430 can be removed from housing 401.

In addition, as shown in FIG. 20B, sensor mounting mechanism 430 can be integrated with housing 401 by engaging mounting part 431 with mounting part 421 in puncturing mechanism 420.

As shown in FIG. 20B, when sensor mounting mechanism 430 is mounted in housing 401, puncturing mechanism 420 has the same function as puncturing mechanism 220 in needle puncturing device 200 shown in FIG. 16.

As described above, according to the present embodiment, needle puncturing device 400 has a configuration in which sensor mounting mechanism 430 is removably mounted in housing 401, and therefore, it is possible to produce the following effects. (1) It is possible to simplify a puncturing needle removing mechanism. (2) It is possible to improve ease of maintenance when blood adheres to sensor mounting mechanism 430. (3) It is possible to reduce the size of an apparatus.

Here, with the present embodiment, a configuration has been adopted where packing 422 is attached to the outer surface of the cylindrical body which faces opening 431a in mounting part 431 in sensor mounting mechanism 430, but, instead of or in addition to this configuration, a packing may be attached to the inner surface of opening 431a in sensor mounting mechanism 430.

Moreover, another configuration may be adopted where a convex part is attached to at least either a mounting surface of mounting part 421 in puncturing mechanism 420 to which mounting part 431 in sensor mounting mechanism 430 is mounted, or a removing surface of mounting part 431 in sensor mounting mechanism 430, which can adhere to the above-described mounting surface. By this means, it is possible to make the mounting surface and the removing surface tightly contact one another, and consequently maintain the airtightness between sensor mounting mechanism 430 and puncturing mechanism 420. In this case, the above-described packing may be used together.

(Embodiment 5)

With Embodiments 5 and 6, a sensor mounting mechanism will be explained.

With embodiment 5, sensor mounting mechanism 130 in needle puncturing device 100 (FIG. 7) according to Embodiment 1 is used as an example for explanation. Likewise, sensor mounting mechanism 430 according to Embodiment 4 is used as an example.

Figure 21C:
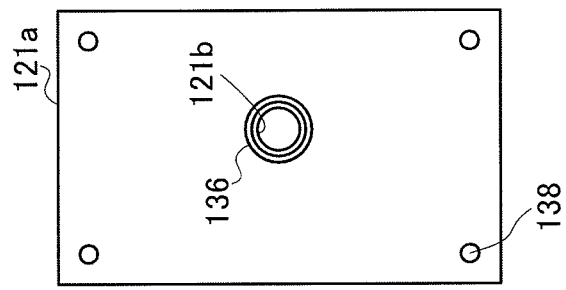
FIG. 21 is a plan view showing a configuration of a sensor mounting mechanism in a blood analysis apparatus according to Embodiment 5 of the present invention.
Figure 21B:
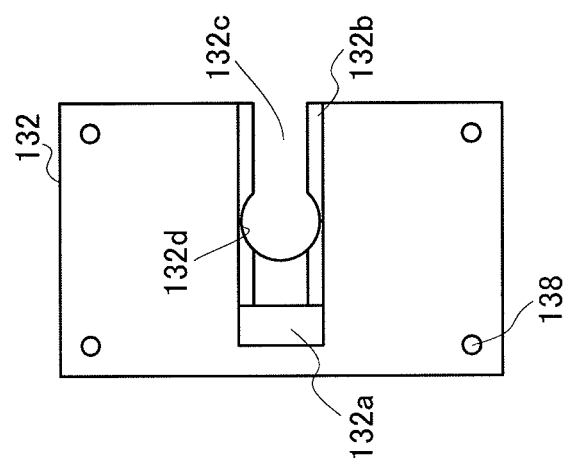
Figure 21A:
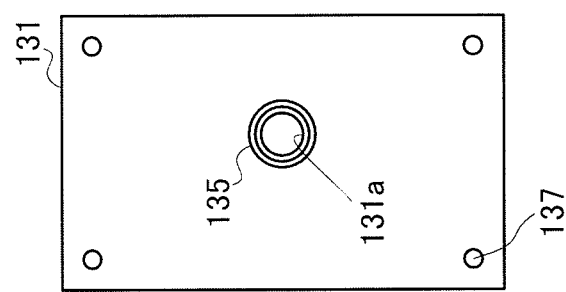

FIG. 21A, FIG. 21B and FIG. 21C (hereinafter collectively referred to as FIG. 21) are top plan views each showing the configuration of sensor mounting mechanism 130 shown in FIG. 7. FIG. 21 shows a state in which skin contacting part 131 (FIG. 21A), sensor holding part 132 (FIG. 21B) and end part 121a (FIG. 21C) are laid out in a plane.

As shown in FIG. 7, sensor mounting mechanism 130 has a configuration to include: skin contacting part 131; sensor holding part 132 to hold sensor 170 in a predetermined position; end part 121a in piston 121 which is the main body of sensor mounting mechanism 130; first spring 133 that biases between skin contacting part 131 and sensor holding part 132 at a first stretching strength; second spring 134 that biases between sensor holding part 132 and end part 121a at a second stretching strength; first packing 135 that seals between skin contacting part 131 and sensor 170 at the time of puncturing; second packing 136 that seals between end part 121a and sensor 170 at the time of puncturing; and moving section holding support 137 (FIG. 21A) that moves and holds skin contacting part 131, sensor holding part 132 and end part 121a.

Moving part holding support 137 (FIG. 21A) is a support part slidably projecting from housing edge 121a, and integrated with rod 118 (FIG. 7). Through-holes 138 (FIG. 21B and FIG. 21C) are open to allow moving part holding support 137 (i.e. rod 118) to slidably pass through in end part 121a and sensor holding part 132, respectively. Moving part holding support 137 (i.e. rod 118) slides through these through-holes 138. In addition, skin contacting part 131 shown in FIG. 21A is attached to the tip of this moving part holding support 137 (rod 118).

End part 121a in piston 121 constitutes sensor mounting mechanism 130.

The end part of skin connecting part 131 is connected to the tip of rod 118 projecting from the apparatus body side. Rod 118 slidably supports sensor 170 by sandwiching and compressing first spring 133 between skin contacting part 131 and sensor holding part 132 and sandwiching and compressing second spring 134 between sensor holding part 132 and end part 121a.

Skin contacting part 131 is made of soft resin (e.g. rubber) in order to improve adhesion to skin.

Spring 126 biases piston 121 at a third stretching strength to return piston 121 to the original state.

Respective stretching strengths of first spring 133, second spring 134 and spring 126 are set as follows.

Spring 126 (third stretching strength)>second spring 134 (second stretching strength)≧first spring 133 (first stretching strength) As shown in FIG. 21A, skin contacting part 131 has opening 131a for puncturing, and ring-like first packing 135 is attached to surround opening 131a.

Sensor holding part 132 shown in FIG. 21B has connector 132a to mount sensor 170, sensor inserting guide 132b that receives sensor 170 and guides it to connector 132a and notch part 132c that cuts out part of sensor holding part 132 in the direction to insert a sensor.

Sensor inserting guide 132b has a function to smoothly mount and remove sensor 170 and prevent measured blood from adhering to a measurement device.

In addition, opening 132d for puncturing is provided in approximately the center part of sensor inserting guide 132b.

Notch part 132c is a cutout part to prevent blood having adhered to sensor 170 from adhering to the inside of a measurement device after measurement.

End part 121a shown in FIG. 21C has opening 121b for puncturing, and ring-like second packing 136 is attached to surround opening 121b.

Figure 22:
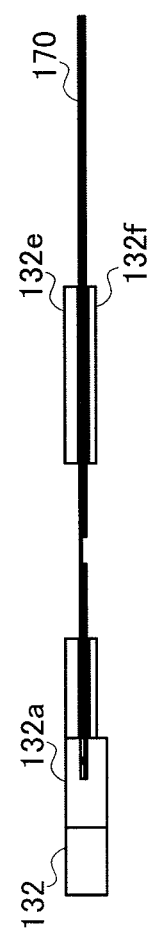
FIG. 22 is a cross sectional view showing a sensor holding part in the sensor mounting mechanism in the blood analysis apparatus according to Embodiment 5.

FIG. 22 is a cross sectional view from the side surface of sensor holding part 132 shows a state in which sensor holding part 132 holds sensor 170.

As shown in FIG. 22, sensor holding part 132 has upper side 132e and lower side 132f sandwiching sensor 170. Lower side 132f is made to be thinner as much as possible. Meanwhile, upper side 132e is formed with a thickness for compensating for decrease in rigidity because lower side 132f is made to be thinner. Lower side 132f of sensor holding part 132 is made to be thinner as much as possible, so that it is possible to suppress unevenness of skin contacting part 131 as much as possible. By this means, skin contacting part 131 can more tightly adhere to skin to improve the reliability of blood sampling, and is applicable to skin of an arm and the back of a hand.

Figure 23:
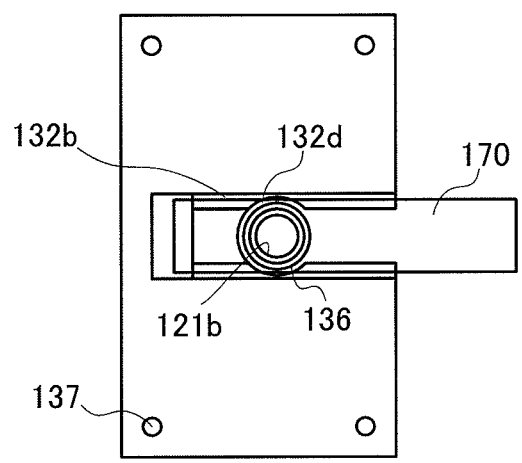
FIG. 23 shows a state in which a sensor is held by the sensor holding part in the sensor mounting mechanism in the blood analysis apparatus according to Embodiment 5.

FIG. 23 is a top plan view showing a state in which sensor 170 is held in sensor holding part 132. FIG. 23 shows a state in which lower end part of sensor 170 is seen through.

As shown in FIG. 23, sensor 170 is inserted and mounted in connector 132a, from notch section 132c (see FIG. 21B) along sensor inserting guide 132b. At this time, sensor 170 moves while being sandwiched between upper side 132e and lower side 132f of sensor holding part 132. This operation is performed by the user holding one end of sensor 170 by hand.

Next, operation of sensor mounting mechanism 130 will be explained.

Figure 24A:
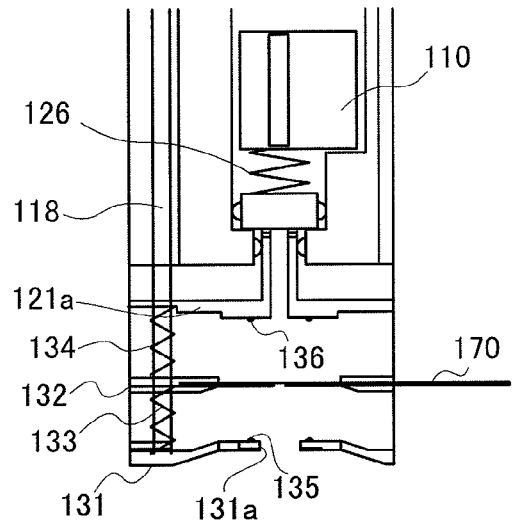
FIGS. 24A, B and C each explain operation of the sensor mounting mechanism in the blood analysis apparatus according to Embodiment 5.
Figure 24B:
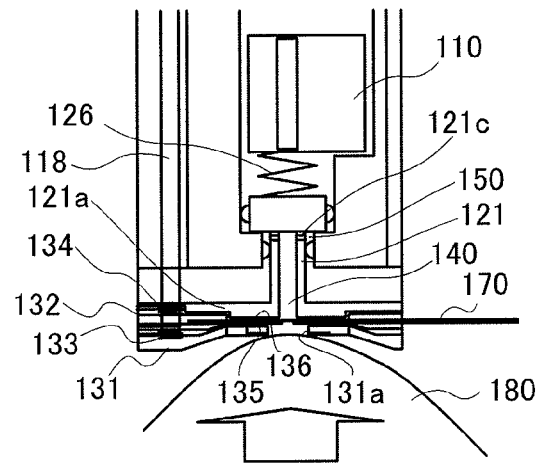
Figure 24C:
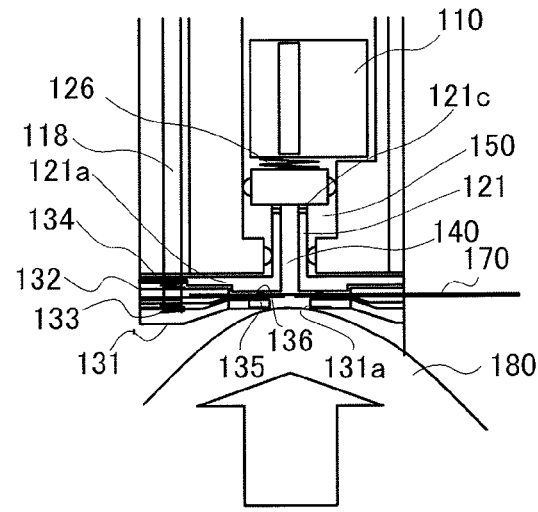

FIG. 24A to FIG. 24C are cross sectional views each showing operation of sensor mounting mechanism 130 at the time of puncturing. In FIG. 24A to FIG. 24C, puncturing operation activating mechanism 110 and sensor mounting mechanism 130 shown in FIG. 7 are simplified.

As shown in FIG. 24A, sensor 170 is mounted in sensor mounting mechanism 130. To be more specific, after checking that sensor mounting mechanism 130 is in the initial state, the user holds one end of sensor 170 by hand and puts the other end of sensor 170 on notch part 132c (see FIG. 21B). Then, the user inserts the other end of sensor 170 from notch part 132c along sensor inserting guide 132b. One end of sensor 170 is placed outside the measurement device and only a reaction part of sensor 170 is inserted.

The other end of sensor 170 is inserted until contacting connector 132a (see FIG. 22), so that mounting sensor 170 in sensor mounting mechanism 130 is completed. Completion of insertion is checked based on the contact between the other end and connector 132a.

Next, as indicated by the arrow shown in FIG. 24B, skin 180 of such as a finger (or palm, upper arm) contacts and pushes skin contacting part 131 in sensor mounting mechanism 130 upward in the direction of the arrow (upward in FIG. 24B).

Here, respective stretching strength of first spring 133, second spring 134 and spring 126 are as follows. Spring 126 (third stretching strength)>second spring 134 (second stretching strength)≧first spring 133 (first stretching strength) Therefore, first spring 133 (first stretching strength), second spring 134 (second stretching strength), and spring 126 (third stretching strength) shrink in this order. Particularly, the stretching strength of each spring is set such that spring 126 (third stretching strength) starts shrinking after first spring 133 (first stretching strength) and second spring 134 (second stretching strength) almost have shrunk. In this case, it is possible to contact skin 180 with sensor 170 more quickly by setting the first stretching strength of first spring 133 to the minimum, in addition to the reason that lower side 132f in sensor holding part 132 is thin. Sensor 170 contacts skin 180 more quickly, so that airtightness is reliably secured more quickly, and therefore it is possible to start puncturing more quickly and improve operability.

Skin contacting part 131 and end part 121a sandwich sensor 170 held in sensor holding part 132 from above and below. First packing 135 and second packing 136 are provided in skin contacting part 131 and end part 121a, and first packing 135 and second packing 136 adhere to sensor 170 following the above-described sandwiching operation. First packing 135 and second packing 136 adhere to sensor 170, so that a part formed by these is tightly sealed. In addition, skin 180 contacting skin contacting part 131 closes opening 131a in skin contacting part 131, so that the airtightness in cylindrical internal space 140 in piston 121 is secured. Moreover, the airtightness in decompression chamber 150 connecting to cylindrical internal space 140 through connection hole 121c is also secured.

Next, as indicated by the arrow in FIG. 24C, skin contacting part 131 is further pushed in the direction of the arrow (upward in FIG. 24C). By this means, the volume of decompression chamber 150 increases and a negative pressure is created in internal space 140, so that it is possible to lift up skin 180.

Next, a variation of each component of sensor mounting mechanism 130 will be explained.

Figure 25:
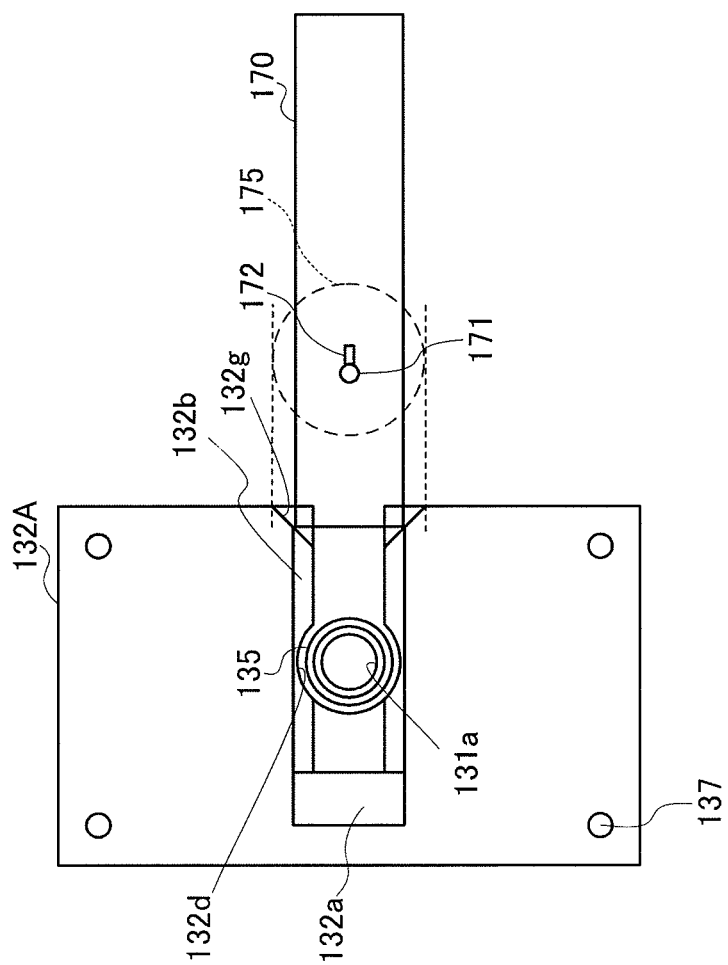
FIG. 25 shows a configuration example of a sensor inserting part in a sensor holding part in the blood analysis apparatus according to Embodiment 5.
Figure 26:
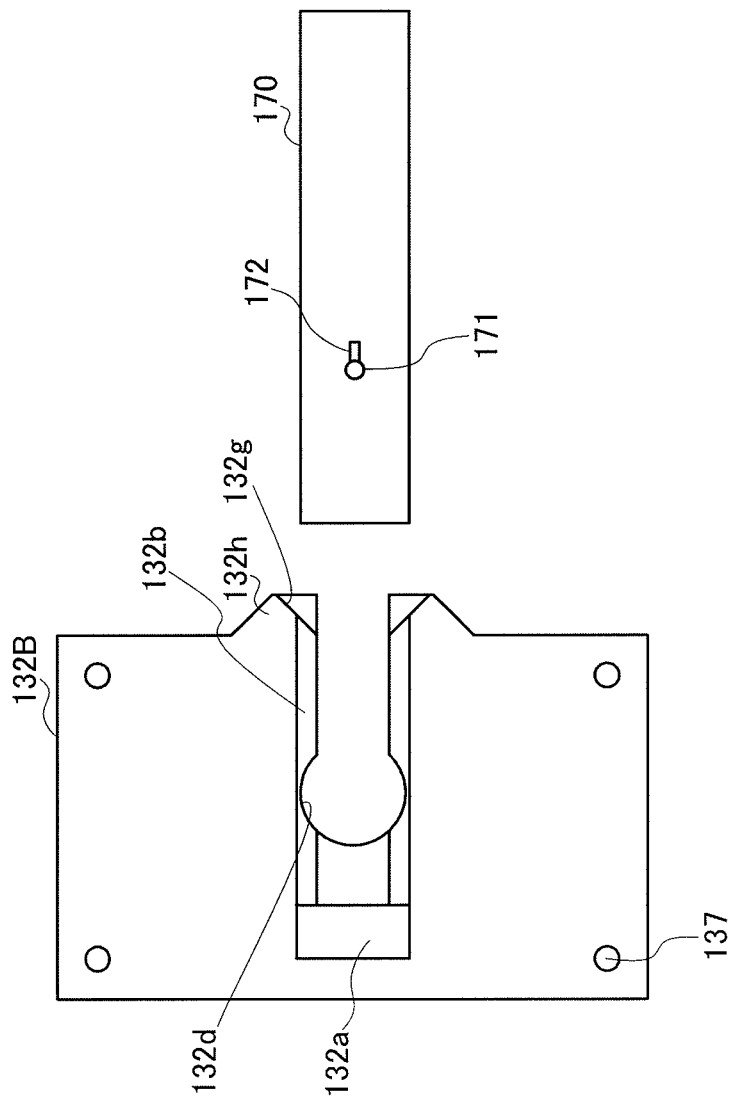
FIG. 26 shows another configuration example of the sensor inserting part in the sensor holding part in the blood analysis apparatus according to Embodiment 5.

FIG. 25 and FIG. 26 each show another configuration example of a sensor inserting part in sensor holding part 132. The same components as in FIG. 21 are assigned the same reference numerals, and overlapping descriptions will be omitted.

As shown in FIG. 25, sensor holding part 132A has guide inlet 132g that guides sensor 170 for ease insertion of sensor 170. With the present embodiment, guide inlet 132g is a linear edge part, but may be a curved edge part.

Guide inlet 132g is formed to have a wide area for ease insertion of sensor 170. For example, guide inlet 132g has faces resulting from cutting off corners, which broaden outward at an angle meeting tangents to the outer periphery of virtual circle 175 indicated by a broken line shown in FIG. 25. Here, virtual circle 175 is greater than the width (in the vertical direction in FIG. 25) of sensor 170, and therefore, guide inlet 132g broadens outward at a certain angle. Here, the maximum width is set to be greater than the width of sensor 170 to ease insertion of sensor 170. The line extending from the above-described certain angle meets a tangent to the outer periphery of virtual circle 175.

In addition, it is preferable to prevent the size of guide inlet 132g from varying until a part to which blood adheres exits a measurement device after sensor 170 is removed from sensor holding part 132A. Here, sensor 170 has puncturing hole 171 and analysis window 172 that allows blood to penetrate through. When puncturing is performed, blood is likely to scatter around these parts.

In addition, as shown in FIG. 26, sensor holding part 132B has convex part 132h in which sensor inserting guide 132b including guide inlet 132g projects outward from the sensor holding part 132B body. By this means, even if the user is a sight-impaired person, it is possible to identify the position to insert sensor 170 by tracing the outer shape of a sensor holding part and consequently correctly mount sensor 170. That is, operability is improved.

As described above, according to the present embodiment, sensor mounting mechanism 130 has a three-layer structure composed of skin contacting part 131, sensor holding part 132 to hold sensor 170 and end part 121a that is the main part of sensor mounting mechanism 130, and includes: first spring 133 that biases between skin contacting part 131 and sensor holding part 132 at a first stretching strength; second spring 134 that biases between sensor holding part 132 and end part 121a at a second stretching strength; first packing 135 that seals between skin contacting part 131 and sensor 170 at the time of puncturing; and second packing 136 that seals between end part 121a and sensor 170 at the time of puncturing. At the time of puncturing, skin 180 contacts skin contacting part 131, and this skin contacting part 131 is pushed up against the biasing force of first spring 133 and second spring 134. By this means, skin contacting part 131, sensor holding part 132 and end part 121a adhere to each other through first packing 135 and second packing 136 to seal internal space 140. After that, skin contacting part 131 is further pushed up against the biasing force of spring 126, so that piston 121 moves into the housing to reduce the pressure in internal space 140.

With the present embodiment, as shown in FIG. 24A to FIG. 24C, reduced pressure space is only internal space 140 connecting to the space surrounded by first packing 135 and second packing 136 in sensor mounting mechanism 130, and therefore the volume of the pressure reduced space is significantly smaller than in conventional examples. Therefore, it is possible to overcome all defects in conventional examples.

To be more specific, reduced pressure space is small, so that it is possible to desirably reduce pressure only by one action, that is, pushing skin contacting part 131. Only one action is required to reduce pressure, so that it is possible to improve operability and ease maintenance. In addition, it is possible to avoid releasing the reduced pressure to return to the atmosphere pressure at an incorrect timing, and therefore, it is possible to prevent blood from scattering due to the unsuccessful pressure release. It is possible to prevent the apparatus from being contaminated and also prevent infection due to the contaminated apparatus.

Moreover, with the present embodiment, sensor 170 can easily be mounted in and removed from sensor mounting mechanism 130, so that it is possible to improve operability for puncturing.

(Embodiment 6)

Figure 27A:
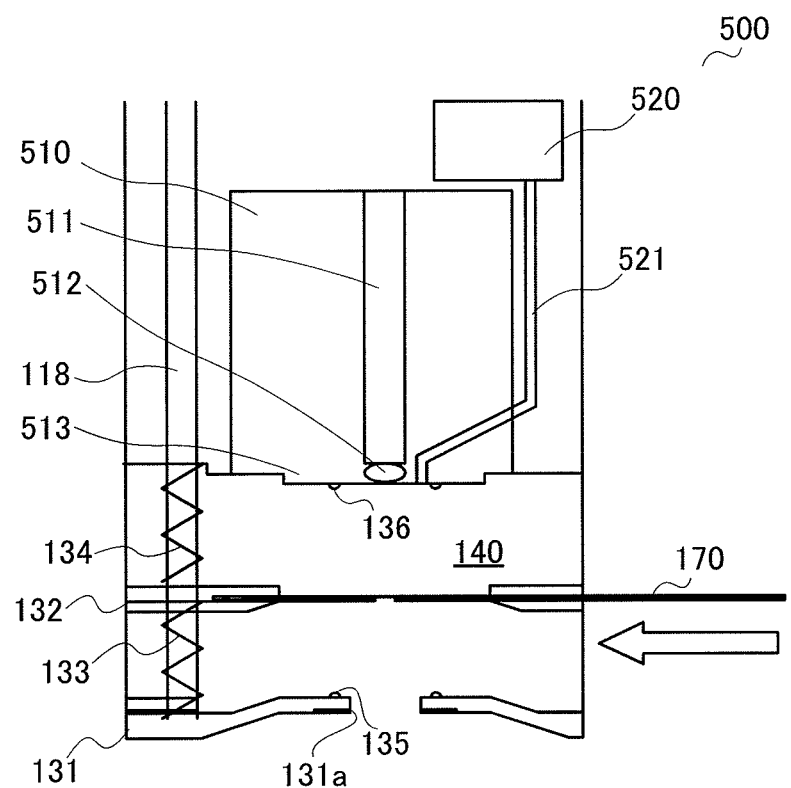
FIGS. 27A and B are cross sectional views each showing a blood analysis apparatus according to Embodiment 6 of the present invention.
Figure 27B:
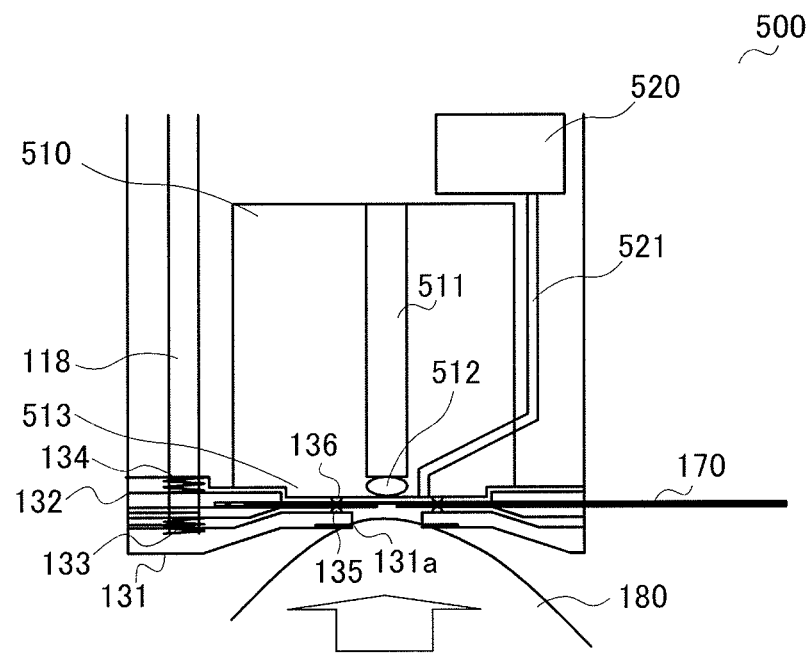

FIG. 27A and FIG. 27B are cross sectional views each showing a blood analysis apparatus according to Embodiment 6 of the present invention. The present embodiment is an example in which sensor mounting mechanism 130 is applied to a blood analysis apparatus with an electric negative pressure pump. In addition, laser puncturing apparatus 510 is applied instead of puncturing operation activating mechanism 110 shown in FIG. 7. The same components as in FIG. 7 are assigned the same reference numerals, and overlapping descriptions will be omitted.

As shown in FIG. 27A and FIG. 27B, blood analysis apparatus 500 has a configuration to mainly include laser puncturing device 510 that punctures skin with laser light without contacting and sensor mounting mechanism 130.

Laser puncturing apparatus 510 has a laser rod that emits laser light, lens 512 that collects laser light for puncturing and bottom 513 facing sensor 170. Second packing 136 surrounding a laser light axis is attached to bottom 513.

Negative pressure pump 520 sucks air in internal space 140 via connection path 521 to reduce the pressure in internal space 140.

As indicated by the arrow shown in FIG. 27A, sensor 170 is mounted in sensor mounting mechanism 130. One end of sensor 170 is inserted to contact connector 132a (see FIG. 22), so that sensor 170 is completely mounted in sensor mounting mechanism 130. It is possible to check completion of insertion by contact between one end of sensor 170 and connector 132a.

As indicated by the arrow shown in FIG. 27B, skin 180 of a finger (or palm, upper arm) contacts skin contacting part 131 and pushes it up.

Skin contacting part 131 and end part 513 sandwich sensor 170 held in sensor holding part 132 from above and below. First packing 135 and second packing 136 are provided on skin contacting part 131 and bottom 513, and first packing 135 and second packing 136 adhere to sensor 170 by the above-described sandwiching operation. In addition, skin 180 contacting skin contacting part 131 closes opening 131a in skin contacting part 131. Moreover, negative pressure pump 520 creates a negative pressure in internal space 140 to lift up skin 180.

As described above, sensor mounting mechanism 130 can be applied to blood analysis apparatus 500 with an electric negative pressure pump, and therefore, it is possible to provide the same effect as in Embodiment 5.

The above description is illustration of preferred embodiments of the present invention and the scope of the invention is not limited to this.

For example, although with the present embodiment, a needle puncturing device that performs puncturing with a puncturing needle is used as a puncturing means, the present invention is not limited to this, and it is possible to use a laser puncturing device as a puncturing means.

Although the name "puncturing device" is used in the embodiments for ease of explanation, "puncturing equipment", "puncturing apparatus" and so forth are possible naturally.

Moreover, the type, the number, the connection method and so forth of components constituting the above-described puncturing device are not limited.

The disclosure of Japanese Patent Application No. 2008-313644, filed on Dec. 9, 2008 and Japanese Patent Application No. 2008-317341, filed on Dec. 12, 2008 including the specifications, drawings and abstracts, are incorporated herein by reference in their entirety.

INDUSTRIAL APPLICABILITY

The decompression mechanism, puncturing apparatus, blood analysis apparatus and sensor mounting mechanism according to the present invention, are useful for a disposal puncturing device having a replaceable puncturing needle for a puncturing device used in blood sampling and a puncturing needle holder that movably accommodates the puncturing needle inside and can be replaced together with the puncturing needle.

REFERENCE SIGNS LIST 100, 200, 300, 400 Needle puncturing device
101, 201, 401 Housing
110, 110A, 110B, 110C Puncturing operation activating mechanism
111 Lancet section
112, 118, 211, 316 Rod
113, 123, 124, 125, 125A, 125B, 134, 212, 213, 422 Packing
114 Puncturing needle holder
120 Decompression and blood sampling mechanism
121, 121A, 121B Piston
122 Cylinder
130, 430 Sensor mounting mechanism
131 Skin contacting part
150, 250 Decompression chamber
160 Puncturing needle
170 Sensor
210 Puncturing operation activating mechanism
215, 315 Knob
220, 420 Puncturing mechanism
230 Decompression mechanism
240 Cylinder block
241 Puncturing mechanism cylinder
242 Decompression mechanism cylinder
241a, 241b, 242a, 242b, 316a, 316b End part
241c Connection hole
315a Bottom
315b, 315c, 431a Opening
350 Puncturing needle removing mechanism
421, 431 Mounting part
500 Blood analysis apparatus

The invention claimed is:

1. A puncturing apparatus comprising:
a housing;
a puncturing section that is provided in the housing and punctures skin;
a puncturing mechanism that operates the puncturing section;
a cylinder having a bottom;
a piston having a first end part projecting from the bottom and a second end part that is located in the cylinder and slides along an axis of the cylinder;
a first sealing section that seals between the bottom and an outer surface of the piston;
a second sealing section that seals between the second end part and an inner surface of the cylinder;
a third sealing section that is located in a joint between the piston and the puncturing mechanism and seals between a hollow space opening in the first end part and the puncturing mechanism; and
an air chamber that is sealed with the first and second sealing sections and surrounded by the outer surface of the piston and the inner surface of the cylinder, wherein the piston has a connection hole that connects the air chamber with the hollow space.

2. The puncturing apparatus according to claim 1, wherein the first sealing section, the second sealing section or the third sealing section is packing.

3. The puncturing apparatus according to claim 1, wherein the first sealing section is a convex part that makes the bottom tightly contact the outer surface of the piston.

4. The puncturing apparatus according to claim 1, wherein the second sealing section is a convex part that makes the second end part tightly contact the inner surface of the cylinder.

5. The puncturing apparatus according to claim 1, wherein the first end part is a contacting part that can contact skin.

6. The puncturing apparatus according to claim 1, wherein the puncturing section is a laser emitting device that punctures skin with laser light.

7. The puncturing apparatus according to claim 1, wherein the puncturing section is a needle puncturing device that punctures skin with a puncturing needle.

8. The puncturing apparatus according to claim 7, further comprising:
a puncturing needle holder that holds the puncturing needle; and
a rod that slides the puncturing needle holder in the piston by puncturing operation of the puncturing mechanism, wherein the third sealing section slides the rod in the piston while keeping the rod airtight.

9. The puncturing apparatus according to claim 8, wherein the third sealing section is packing and adheres to the puncturing needle holder at a time of pressure reduction.

10. The puncturing apparatus according to claim 8, wherein the third sealing section is elastically deformable packing and deforms to wrap around the puncturing needle holder at a time of pressure reduction.

11. The puncturing apparatus according to claim 8, wherein:
   the third sealing section is packing; and
   the packing or the puncturing needle holder has a ring-like convex part on a surface adhering to the packing.

12. The puncturing apparatus according to claim 8, wherein:
   the third sealing section is packing; and
   the puncturing needle holder has a sucker structure on a surface adhering to the packing.

* * * * *